(12) United States Patent
Sakata et al.

(10) Patent No.: US 7,470,238 B2
(45) Date of Patent: Dec. 30, 2008

(54) UNIT FOR PIERCING, AND PIERCING DEVICE

(75) Inventors: Tetsuya Sakata, Kyoto (JP); Daisuke Matsumoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 216 days.

(21) Appl. No.: 10/519,892

(22) PCT Filed: Jul. 1, 2003

(86) PCT No.: PCT/JP03/08383

§ 371 (c)(1),
(2), (4) Date: Dec. 29, 2004

(87) PCT Pub. No.: WO2004/004565

PCT Pub. Date: Jan. 15, 2004

(65) Prior Publication Data

US 2006/0047220 A1 Mar. 2, 2006

(30) Foreign Application Priority Data

Jul. 2, 2002 (JP) ............... 2002-193844
Jul. 2, 2002 (JP) ............... 2002-193845
Jul. 29, 2002 (JP) ............... 2002-220052

(51) Int. Cl.
*A61B 5/00* (2006.01)
*A61B 17/32* (2006.01)

(52) U.S. Cl. ..................... 600/583; 606/182
(58) Field of Classification Search ............... 600/583, 600/584; 606/181, 182, 183
See application file for complete search history.

(56) References Cited

U.S. PATENT DOCUMENTS

| | | | | |
|---|---|---|---|---|
| 4,469,110 A | * | 9/1984 | Slama | 600/583 |
| 5,554,166 A | * | 9/1996 | Lange et al. | 606/182 |
| 5,741,288 A | * | 4/1998 | Rife | 606/181 |
| 5,797,942 A | * | 8/1998 | Schraga | 606/182 |
| 5,871,494 A | * | 2/1999 | Simons et al. | 606/181 |
| 6,036,924 A | * | 3/2000 | Simons et al. | 422/100 |
| 6,315,738 B1 | | 11/2001 | Nishikawa et al. | |
| 6,849,052 B2 | * | 2/2005 | Uchigaki et al. | 600/584 |
| 2003/0109808 A1 | | 6/2003 | Takinami et al. | |
| 2003/0144608 A1 | * | 7/2003 | Kojima et al. | 600/583 |

FOREIGN PATENT DOCUMENTS

| | | |
|---|---|---|
| EP | 1 238 632 | 9/2002 |
| JP | 5-88503 | 12/1993 |
| JP | 7-16218 | 1/1995 |
| JP | 2001-74731 | 3/2001 |
| JP | 01/41643 | 6/2001 |
| JP | 2002-34956 | 2/2002 |
| WO | WO0141643 A1 * | 6/2001 |

* cited by examiner

*Primary Examiner*—Max Hindenburg
*Assistant Examiner*—Sharick Naqi
(74) *Attorney, Agent, or Firm*—Hamre, Schumann, Mueller & Larson, P.C.

(57) ABSTRACT

A lancing unit (U1) includes a lancing member (2), an auxiliary part (3) which is separate from the lancing member (2), and a supporter (1) detachably supporting these. Preferably, the lancing unit (U1) further includes a cap (29) which covers a needle (21) of the lancing member (2) and which is detachable from the lancing member (2), and the lancing member (2) is supported by the supporter (1) via the cap (29).

15 Claims, 24 Drawing Sheets

UNIT FOR PIERCING, AND PIERCING DEVICE

TECHNICAL FIELD

The present invention relates to a lancing apparatus used to extract body fluid such as blood. It also relates to a lancing unit holding a disposable part as a unit and used as mounted to such a lancing apparatus.

BACKGROUND ART

For diabetes treatment, management of the blood glucose level by a patient himself or herself is important for maintaining the blood glucose level in a normal range. Particularly, for a patient of insulin-dependent diabetes, regular measurement of the blood glucose level is essential to maintain the blood glucose level in a normal range. However, it is troublesome to often go to a medical institution for measuring the blood glucose level. Conventionally, therefore, apparatuses which enable the extraction and analysis of blood without going to a medical institution have been proposed. For example, JP-A 2001-74731 discloses a lancing unit and a lancing apparatus as shown in FIGS. 26A and 26B.

The lancing unit 9 shown in FIG. 26A includes a lancet 90 as a lancing member, and a first housing 91A accommodating part of the lancet. The first housing 91A is fixedly fitted to a second housing 91B. As shown in FIG. 26B, the second housing 91B is provided with a test strip 92 and a blood introduction portion 95. The first housing 91A has an opening 91a which is closed by a cover 93 so that a sterilized needle 90a of the lancet 90 can be kept hygienically clean. The first and the second housings 91A and 91B are wrapped by a wrapping member 94 in the form of a bag or case.

The lancing unit 9 having the above-described structure is assembled by setting the needle 90a of the lancet 90 into the first housing 91A after the needle 90a is sterilized and then fixing the first housing 91A to the second housing 91B. With such an assembling method, the sterilization of the lancet 90 can be performed independently without adversely affecting the test piece 92. For example, unlike the above, when the sterilization of the lancet 90 is performed after the lancing unit 9 is completely assembled, a constituent of the test piece 92 may be unduly changed due to the sterilization process. With the above assembling method, however, such a problem can be avoided.

As shown in FIG. 26B, the lancing apparatus 8 includes a housing case 80. The first and the second housings 91A and 91B can be mounted to the apparatus when they are pushed to a front end 80a of the housing case 80. Therefore, the lancet 90 and the test piece 92 can be mounted simultaneously. When the lancet 90 pushes a lancet holder 81 to the right in the figure, a spring 82 is compressed to bring the lancing apparatus 8 into a locked state. Thereafter, when an operation switch 83 is operated with the lancing apparatus 8 pressed against the skin of a human body, the lancet holder 81 and the lancet 90 advance to the left in the figure due to the resilient force of the spring 82, whereby the needle 90a of the lancet 90 lances the skin of the human body. The blood bleeding from the skin as a result of the lancing is introduced to the test sheet 92 through the blood introducing portion 95. The blood can be analyzed by optically detecting the color reaction of the test piece 92.

However, the above-described prior art arrangement has the following problems.

First, in the prior art arrangement, to mount the lancet 90 and the test piece 92 to the lancing apparatus 8, both of the first and the second housings 91A and 91B of the lancing unit 9 need be mounted to the lancing apparatus 8. Therefore, the front end of the lancing apparatus 8 needs to be made relatively large. As a result, the size of the lancing apparatus 8 increases, which is inconvenient for carrying.

Secondly, from a hygienic point of view, the needle 90a of the lancet 90 need be hermetically sealed in the first housing 91A of the lancing unit 9. For this purpose, the portion where the first housing 91A and the lancet 90 are fitted together need be hermetically sealed. On the other hand, after the first housing 91A along with the lancet 90 is mounted to the lancing apparatus 8 and the lancet holder 81 is advanced, the lancet 90 needs to move smoothly relative to the first housing 91A in accordance with the movement of the lancet holder. However, to hold the lancet 90 in the first housing 91A in such a manner as to satisfy the above two requirements is not easy. Thus, the needle 90a of the lancet 90 sometimes is not hermetically sealed, or the lancet 90 after it is mounted to the lancing apparatus 8 sometimes does not move smoothly.

Thirdly, in the lancing apparatus 8, it is desirable that the blood introduction portion 95 is located as close to the lancing position as possible. This is because, as the blood introduction portion 95 is farther from the lancing position, the blood is less likely to come into contact with the blood introduction portion 95 properly. Even when the blood comes into contact with the blood introduction portion 95, the amount of blood reaching the test piece 92 is small, whereby accurate analysis result may not be obtained. Since the first case 91A is fixed to the housing 80 while the lancet 90 moves reciprocally along a predetermined path, the distance s between the path and the blood introduction portion 95 is always constant. In the prior art arrangement, therefore, to locate the blood introduction portion 95 close to the lancing position, the blood introduction portion 95 need be provided close to the needle 90a of the lancet 90 in the state of the lancing unit 9 shown in FIG. 26A (though this figure does not show the blood introduction portion). However, in actually designing and manufacturing the lancing unit 9, various points need be taken into consideration such as reduction in size of the entire unit and the airtightness of the first case 91A, so that it is sometimes difficult to locate the blood introduction portion 95 sufficiently close to the needle 90a of the lancet 90. Therefore, in the prior art arrangement, it is difficult to locate the blood introduction portion 95 sufficiently close to the lancing position, so that the amount of blood introduced to the test piece 92 is sometimes insufficient.

Fourthly, since the lancing unit 9 requires the cover 93 in addition to the first and the second housings 91A and 91B, the number of parts of the lancing unit 9 is large, whereby the manufacturing cost is relatively high.

DISCLOSURE OF THE INVENTION

An object of the present invention is to provide a lancing unit and a lancing apparatus which are capable of eliminating or lessening the above-described problems.

According to a first aspect of the present invention, there is provided a lancing unit comprising a lancing member, an auxiliary part which is separate from the lancing member, and a supporter detachably supporting each of the lancing member and the auxiliary part.

In the present invention, the lancing member and the auxiliary part may not be directly supported by the supporter but may be indirectly supported by the supporter.

Preferably, the auxiliary part comprises a part for taking a sample obtained by lancing. The auxiliary part may be provided with a reagent for undergoing reaction with the sample.

Preferably, when lancing of a skin is performed by utilizing the lancing member, the auxiliary part engages the lancing member to control lancing depth in the skin.

Preferably, the lancing member includes a needle, and the lancing unit of the present invention further comprises a cap for covering the needle. The cap is detachable from the lancing member.

Preferably, the lancing member includes a body holding the needle, and the cap is integrally formed on the body.

Preferably, the boundary portion between the cap and the body has a structure which causes a stress to be concentrated on the boundary portion more than on other portions of the cap and the body.

Preferably, the boundary portion has a constricted configuration.

Preferably, the lancing member is supported by the supporter via the cap.

Preferably, the cap is formed separately from the supporter and supported by the supporter.

Preferably, the supporter includes a portion for fitting to a part of the cap to hold the cap in a standing posture.

Preferably, the cap is integrally formed on the supporter.

Preferably, the supporter comprises a case including a tubular portion at least one end of which is open, and the case accommodates the lancing member, the cap, and the auxiliary part. The tubular portion is not limited to one having a circular cross section but may be one having a square or rectangular cross section with flat side surfaces.

Preferably, the lancing unit according to the present invention further comprises a lid for closing the open end of the case.

Preferably, the direction in which the auxiliary part is detachable from the supporter corresponds to the direction in which the cap is detachable from the lancing member.

Preferably, the auxiliary part is detachably supported by the cap.

Preferably, the cap is supported by the supporter while being interposed between the lancing member and the auxiliary part in a first direction in which the needle of the lancing member extends, and the cap is movable in a second direction crossing the first direction to avoid overlapping with the auxiliary part in the first direction.

Preferably, the supporter includes an arm portion for supporting the cap, and the arm portion is deformable in the second direction.

Preferably, the arm portion is provided by forming a cutout in the supporter.

Preferably, the auxiliary part includes a surface facing the cap, and the surface is inclined at least partially to be oriented also in the second direction.

According to a second aspect of the present invention, there is provided a lancing apparatus for performing lancing by utilizing a lancing unit including a lancing member, an auxiliary part and a supporter detachably supporting the lancing member and the auxiliary part. The apparatus comprises a first holder for holding the lancing member, a moving mechanism for advancing the first holder in a predetermined direction when a predetermined operation is performed, and a second holder for holding the auxiliary part when the lancing member is held by the first holder.

According to a third aspect of the present invention, there is provided a lancing apparatus comprising a moving mechanism for holding a lancing member and advancing the lancing member in a first direction, and a holding portion for arranging and holding an auxiliary part at a position spaced from a path of the advancing movement of the lancing member in a second direction crossing the first direction. At least one of the auxiliary part and the lancing member is movable in the second direction.

Preferably, the holding portion is capable of moving the auxiliary part in the second direction.

Preferably, the moving mechanism detachably holds the lancing member, and a cap for covering a needle of the lancing member is attached to the lancing member. The holding portion is capable of moving the auxiliary part toward the advancing movement path of the lancing member when the cap is separated from the lancing member with the lancing member held by the moving mechanism.

Preferably, the holding portion includes a first wall, a second wall located closer to the advancing movement path of the lancing member than the first wall, a space defined between the first and the second walls into which the auxiliary part can be partially inserted movably in the second direction, and a resilient member for pressing a portion of the auxiliary part toward the second wall when the auxiliary part is partially inserted into the space.

Preferably, in the lancing apparatus according to the present invention, when the lancing member advances, the lancing member engages the auxiliary part so that the advancing movement of the lancing member is controlled.

Preferably, the holding portion allows movement of the auxiliary part in a direction opposite from the first direction when the auxiliary part receives a force in said direction.

Preferably, the lancing apparatus according to the present invention further comprising a measurement probe, and the auxiliary part includes an electrode for analyzing a sample obtained by lancing. The measurement probe is brought into contact with the electrode as a result of movement of the auxiliary part toward the advancing movement path of the lancing member.

Preferably, the lancing apparatus according to the present invention further comprises a control circuit for executing analysis of the sample.

Other features and advantages of the present invention will become clearer from the description of the embodiments given below.

BRIEF DESCRIPTION OF THE DRAWINGS

FIG. 5A is a perspective view showing a sensor incorporated in the lancing unit of FIG. 1, whereas

FIG. 26A is a sectional view showing a prior art lancing unit, whereas

BEST MODE FOR CARRYING OUT THE INVENTION

Figure 1:
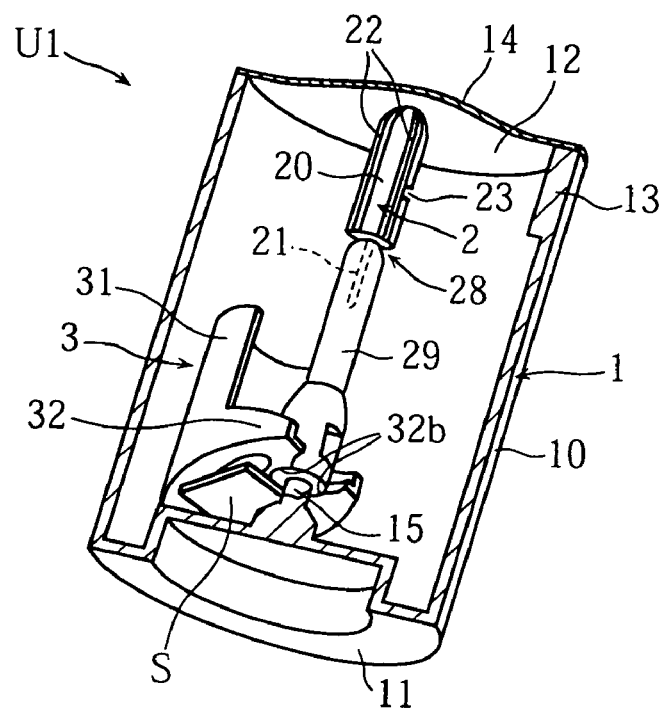
FIG. 1 is a perspective view, partially cut away, showing an example of lancing unit according to the present invention.

Preferred embodiments of the present invention will be described below in detail with reference to the accompanying drawings.

FIGS. 1-6 show an example of lancing unit and the structural parts according to the present invention. As better shown in FIGS. 1 and 2, the lancing unit U1 in this embodiment includes a case 1, a lancet 2, a cap 29 and a sensor holder 3.

The case 1 is an example of supporter according to the present invention. The case 1, which is made of synthetic resin, includes a generally cylindrical tubular portion 10 having an end (upper end) formed with an opening 12, and a bottom portion 11 connected to another end (lower end) of the tubular portion 10. The tubular portion 10 has an inner circumferential surface formed with a projection 13, which serves as a rotation stopper in fitting the case 1 around a part of a lancing apparatus A1, which will be described later. A film 14 as a lid for closing the opening 12 is bonded to the upper surface of the case 1, whereby the case 1 is hermetically closed. As the film 14, use may be made of one made of an aluminum foil or one provided by laminating a resin film onto an aluminum foil.

Figure 3A:
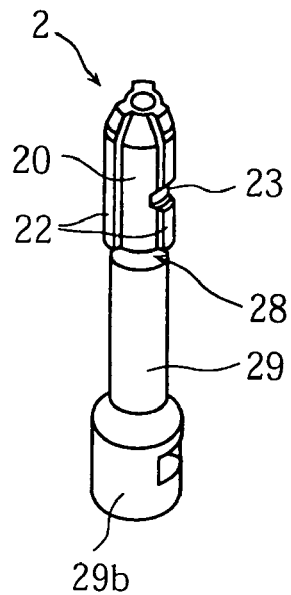
FIG. 3A is a perspective view showing a lancet with a cap incorporated in the lancing unit shown in FIG. 1.
Figure 3B:
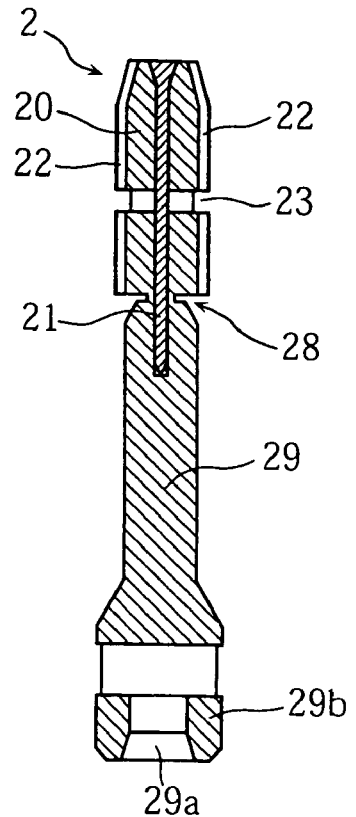
FIG. 3B is a sectional view thereof.

As better shown in FIGS. 3A and 3B, the lancet 2 includes a needle 21 made of metal, and a body 20 made of synthetic resin and holding the needle 21. The body 20 is so configured as to be properly mounted to a lancet holder 5 of the lancing apparatus A1, which will be described later, and formed with a plurality of ribs 22 extending in the same direction as the needle 21 and a recess 23.

The cap 29, which is formed integrally on the body 20 by resin molding, covers the front end of the needle 21 projecting from the body 20 and extends on the front end side (lower end side) of the body 20 in the same direction as the needle 21. The boundary portion 28 between the cap 29 and the body 20 is constricted to be smaller in diameter than other portions. The boundary portion 28 is constricted so that the boundary portion 28 break due to stress concentration on that portion when e.g. a torsional force is exerted to the cap 29 and the body 20. As means for causing the stress to be concentrated on the boundary portion 28, instead of making the boundary portion 28 constricted, a plurality of circumferentially spaced recesses of a depth which does not expose the needle 21 may be formed at the boundary portion 28.

Figure 6:
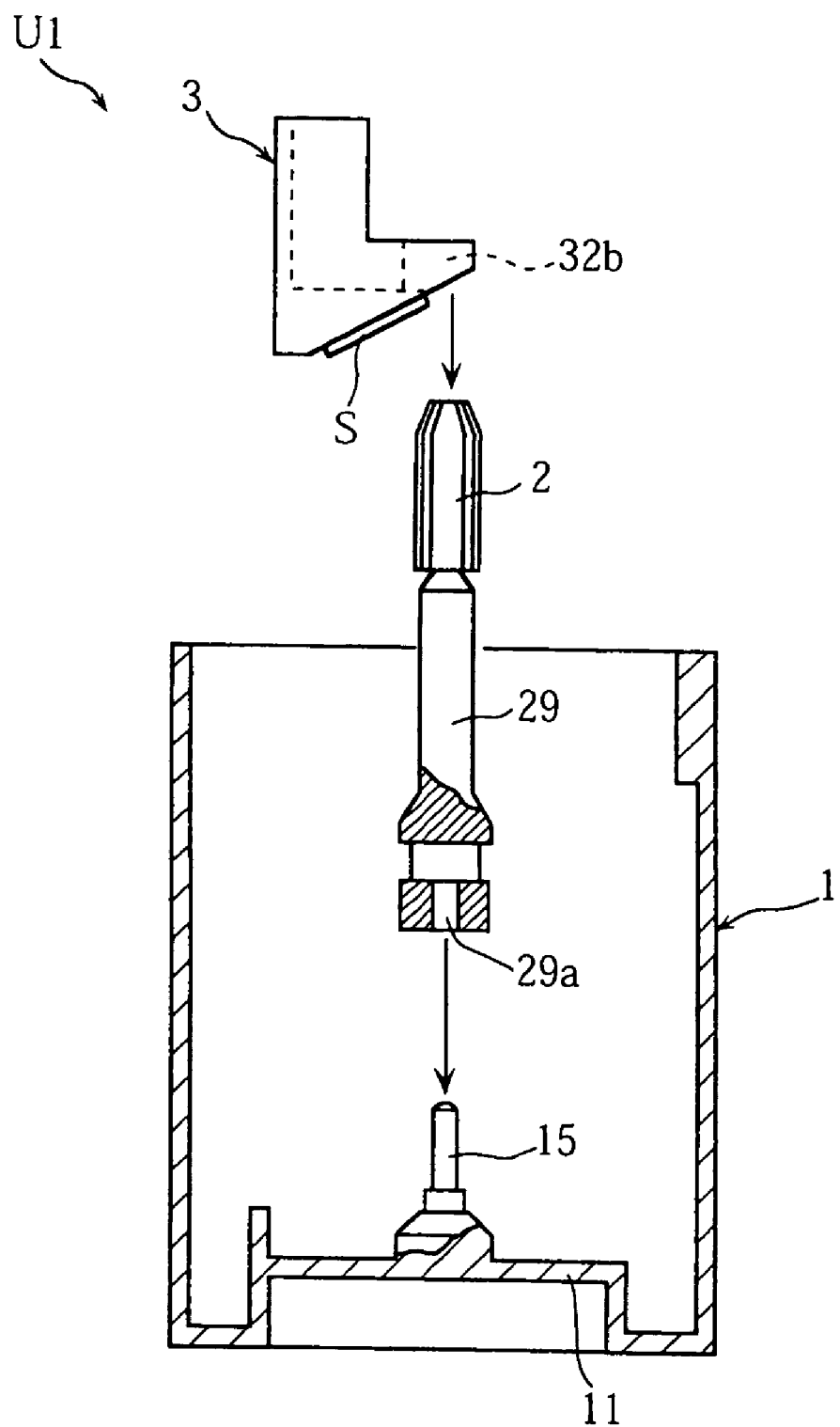
FIG. 6 is an exploded view, partially in section, of the lancing unit shown in FIG. 1.

The cap 29 has a lower end formed with a hole 29a. As shown in FIG. 6, the hole 29a can be fitted to a projection 15 projecting from the bottom portion 11 of the case 1. By the fitting, the cap 29 is held in the case 1 in a standing posture. In the present invention, conversely to the above structure, the bottom portion 11 of the case 1 may be formed with a recess, whereas the bottom of the cap 29 may be formed with a projection to be fitted in the recess. The cap 29 is bonded to the case 1 with an adhesive. Instead of using an adhesive, the bonding may be performed by ultrasonic welding or thermal fusing. This holds true for the bonding between other portions of the lancing unit. The needle 21 of the lancet 2 is subjected to sterilization by e.g. γ-ray irradiation before it is incorporated into the case 1. Preferably, in the case 1 is further disposed a desiccant (not shown) for keeping the quality of a sensor S, which will be described later.

The sensor holder 3 is an example of auxiliary part of the present invention. As better shown in FIG. 4, the sensor holder 3, which is made of synthetic resin, includes a main body 32 and a projecting wall 31 projecting upward from the main body 32 and having an arcuate cross section. The main body 32 has a bottom surface which is inclined, for example, and to which the sensor S is attached.

Figure 5A:
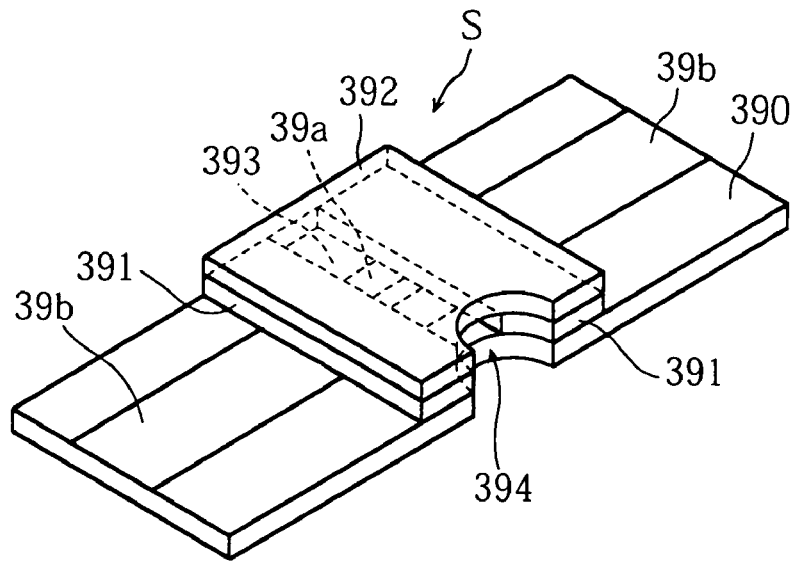
Figure 5B:
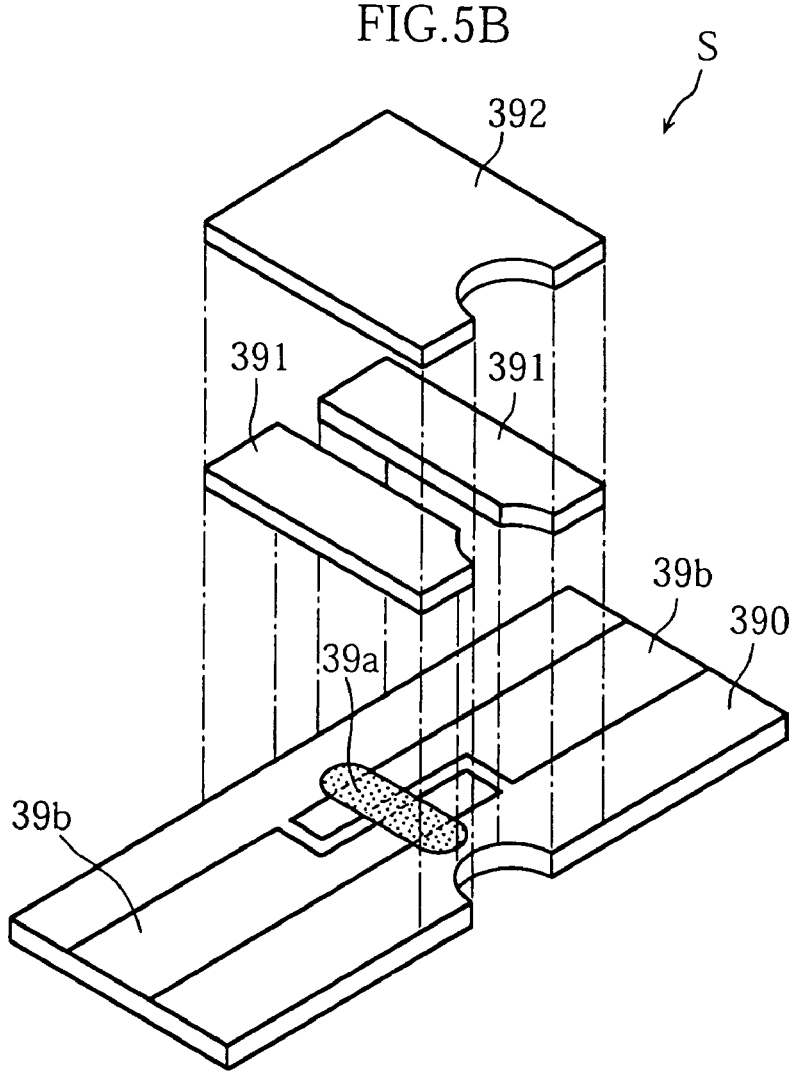
FIG. 5B is an exploded perspective view of the sensor.

The sensor S is in the form of a chip and has a structure as shown in FIGS. 5A and 5B, for example. The sensor S includes a substrate 390 on which are provided a reagent 39a containing enzyme which undergoes certain reaction (e.g. oxidation reaction) with glucose in blood, and a pair of electrodes 39b for electrically detecting the degree of the reaction. On the substrate 390 are also provided a pair of spacers 391 spaced from each other, and a cover 392 for covering the spacers 391, all of which serve to define a capillary 393. The substrate 390, each of the spacers 391 and the cover 392 are continuously formed with a recess 394 which serves as a blood introduction port. When blood is applied to the recess 394, the blood travels through the capillary 393 by capillary action and is guided to the reagent 39a.

Figure 2:
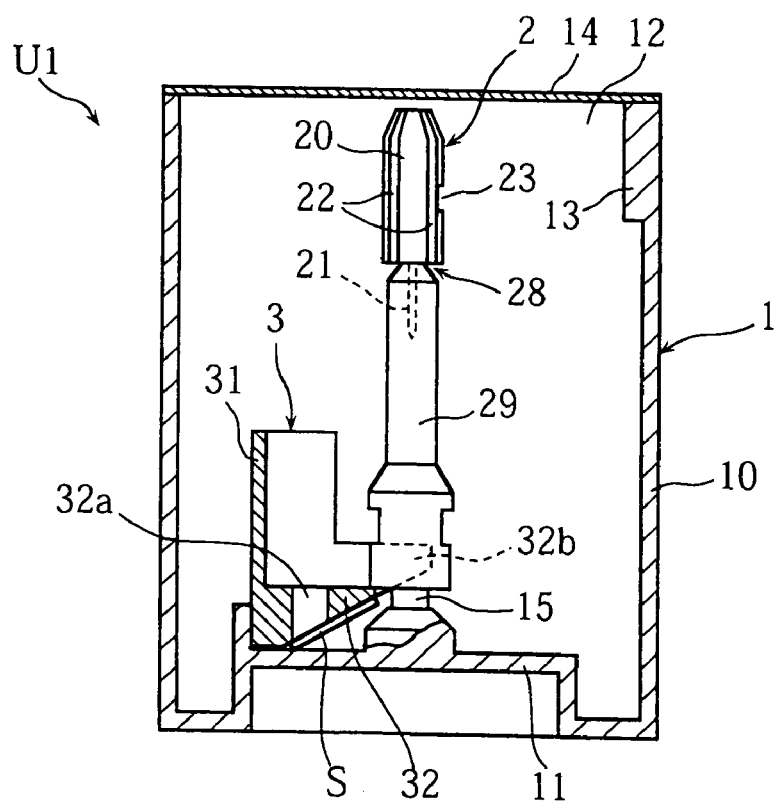
FIG. 2 is a side sectional view of FIG. 1.
Figure 4:
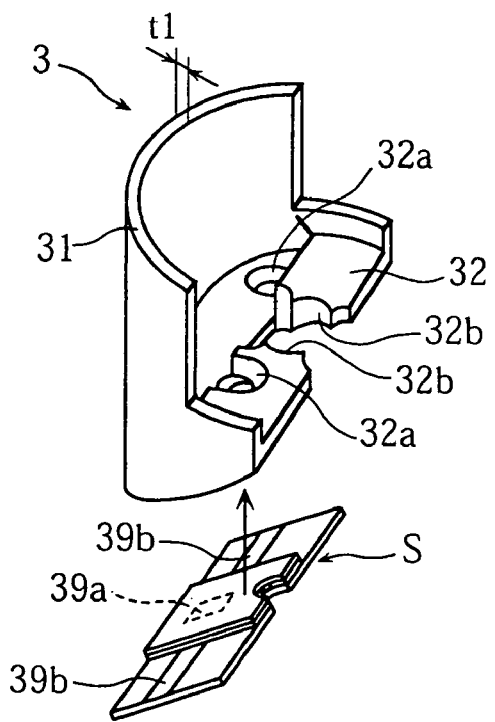
FIG. 4 is a perspective view showing a sensor holder incorporated in the lancing unit of FIG. 1.

As shown in FIG. 4, the main body 32 of the sensor holder 3 is formed with a pair of through-holes 32a and a pair of holding walls 32b. The paired through-holes 32a are utilized for inserting a pair of measurement probes 62 of the lancing apparatus A1, which will be described later, to bring the measurement probes 62 into contact with the paired electrodes 39b of the sensor S. The paired holding walls 32b can be fitted around a lower portion 29b of the cap 29 so as to clip the lower portion from opposite sides. For example, the lower portion 29b of the cap 29 is columnar, whereas the paired holding walls 32b are curved into a generally arcuate shape corresponding to the circumferential surface of the lower portion. As shown in FIGS. 1 and 2, by fitting the paired holding walls 32b around the lower portion of the cap 29, the sensor holder 3 is attached to the case 1 via the cap 29. However, the sensor holder 3 is slidable upward for detachment from the cap 29.

Figure 7:
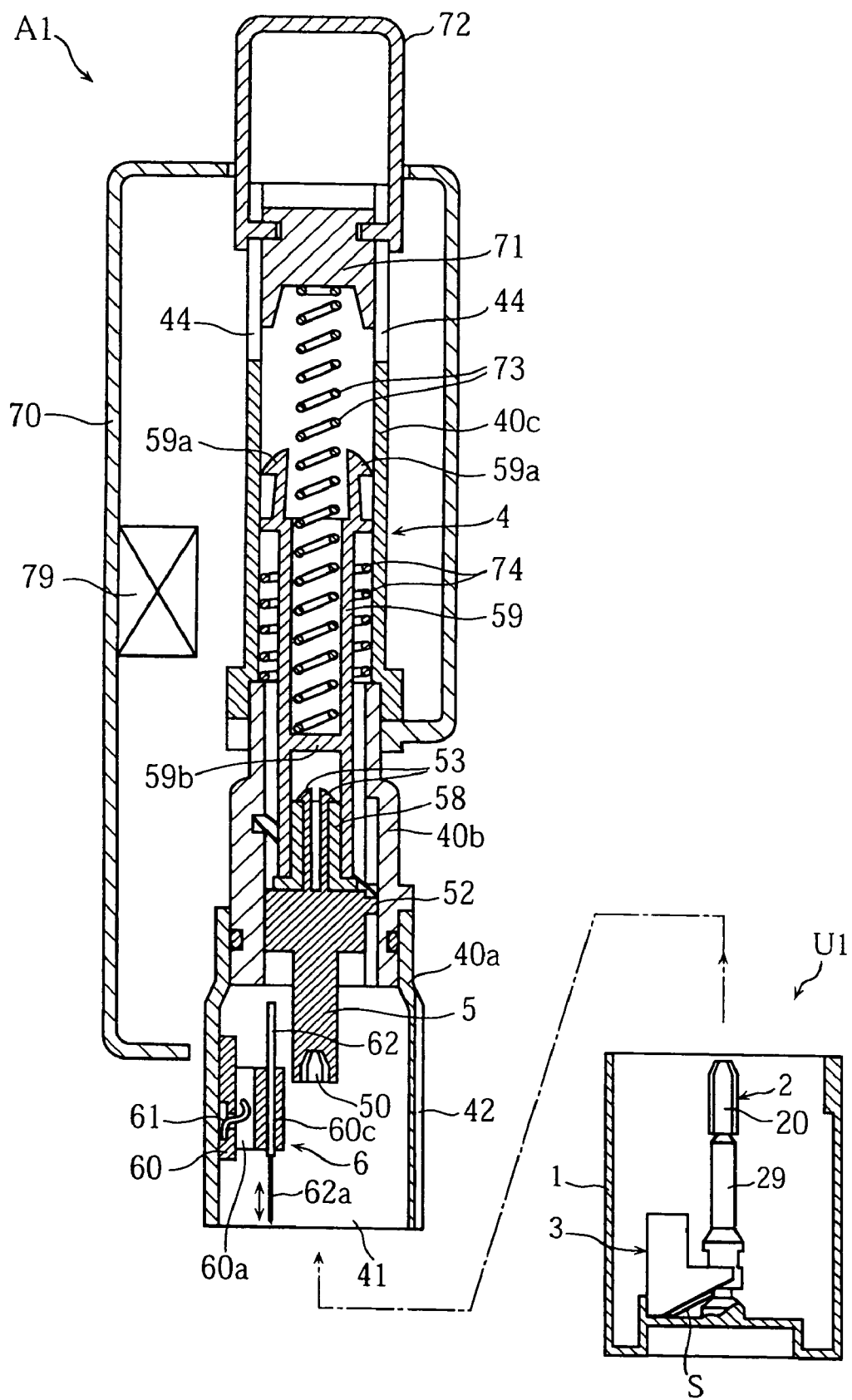
FIG. 7 is a sectional view showing an example of lancing apparatus according to the present invention.

FIG. 7 shows an example of lancing apparatus suitable for using the above lancing unit U1.

As shown in the figure, the lancing apparatus A1 of this embodiment includes a housing 4, a lancet holder 5 arranged in the housing 4, a latch member 59 and a holding portion 6.

Figure 11:
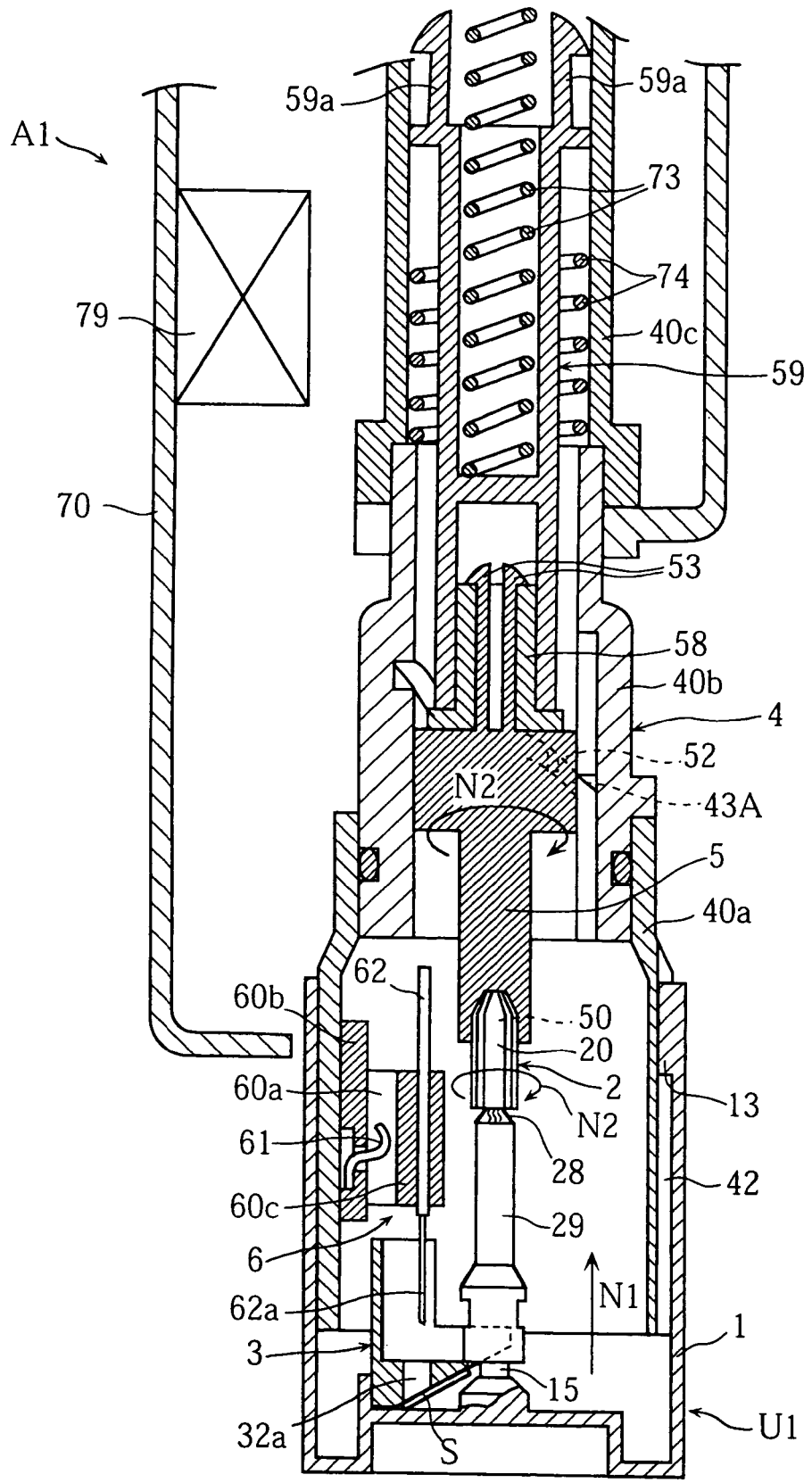
FIG. 11 is a sectional view of a principal portion in the process of mounting the lancet and the sensor holder of the lancing unit shown in FIG. 1 to the lancing apparatus shown in FIG. 7.

The housing 4 is provided by connecting three sleeves 40a-40c constituting a front end portion, an intermediate portion, and a rear end portion in series and is fixed to an outer case 70. The sleeve 40a has a front end (lower end) which comes into contact with the skin of a human body in performing lancing and which has an opening 41. As shown in FIG. 11, the sleeve 40a has a configuration and a size which make it possible to fit the case 1 of the lancing unit U1 to the sleeve by sliding. The sleeve 40a has an outer surface formed with a groove 42 for receiving the projection 13 of the case 1. The groove 42 extends longitudinally of the sleeve 40a to prevent the rotation of the case 1 in fitting the case 1 around the sleeve 40a. In the lancing apparatus A1, the lancet 2 and the sensor holder 3 of the lancing unit U1 are mounted to the lancing apparatus A1 by sliding and fitting the case 1 around the sleeve 40a, whereby the lancet 2 and the sensor holder 3 are precisely guided to predetermined positions in the lancing apparatus A1, which will be described later.

Figure 12:
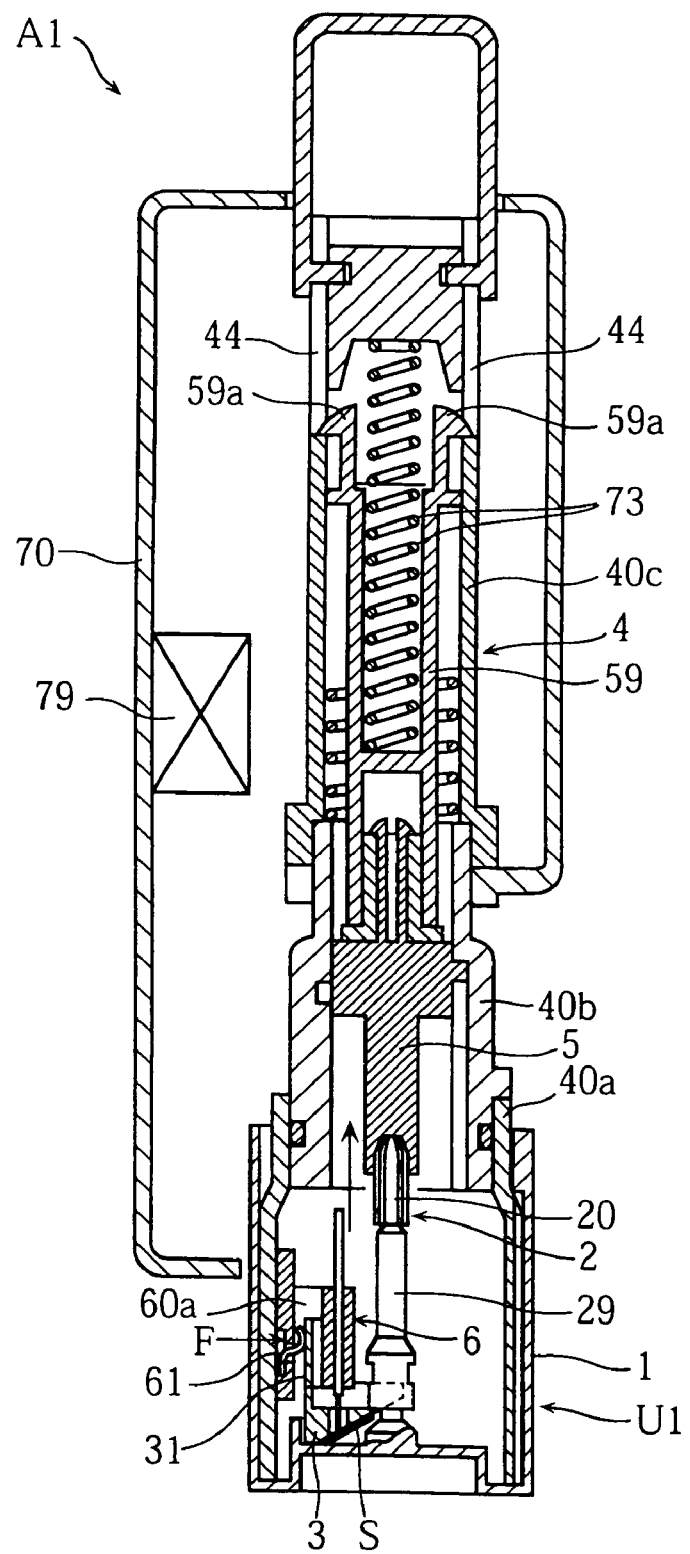
FIG. 12 is a sectional view showing the process of mounting the lancet and the sensor holder of the lancing unit shown in FIG. 1 to the lancing apparatus shown in FIG. 7.
Figure 13:
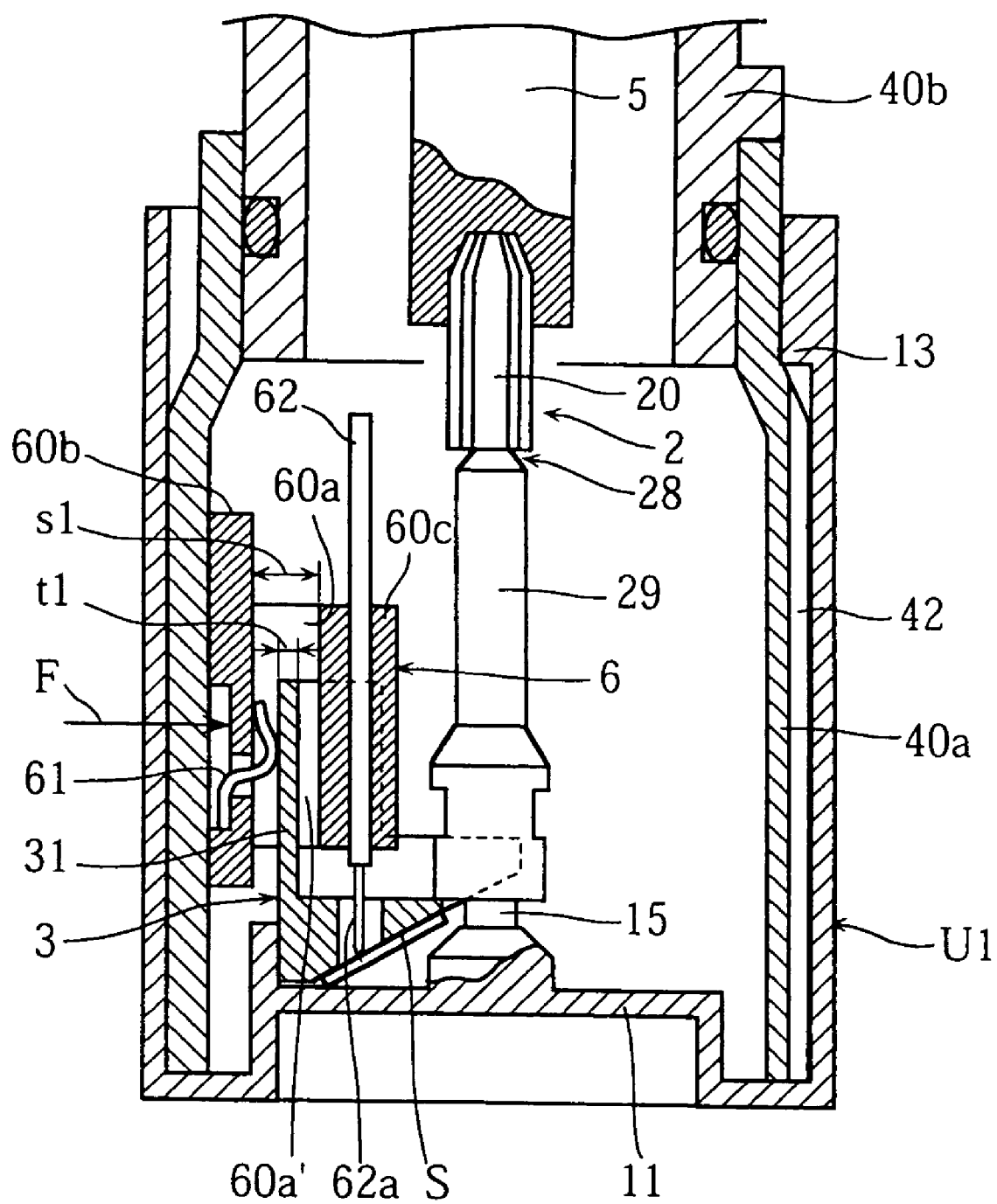
FIG. 13 is a sectional view showing a principal portion of FIG. 12.
Figure 14:
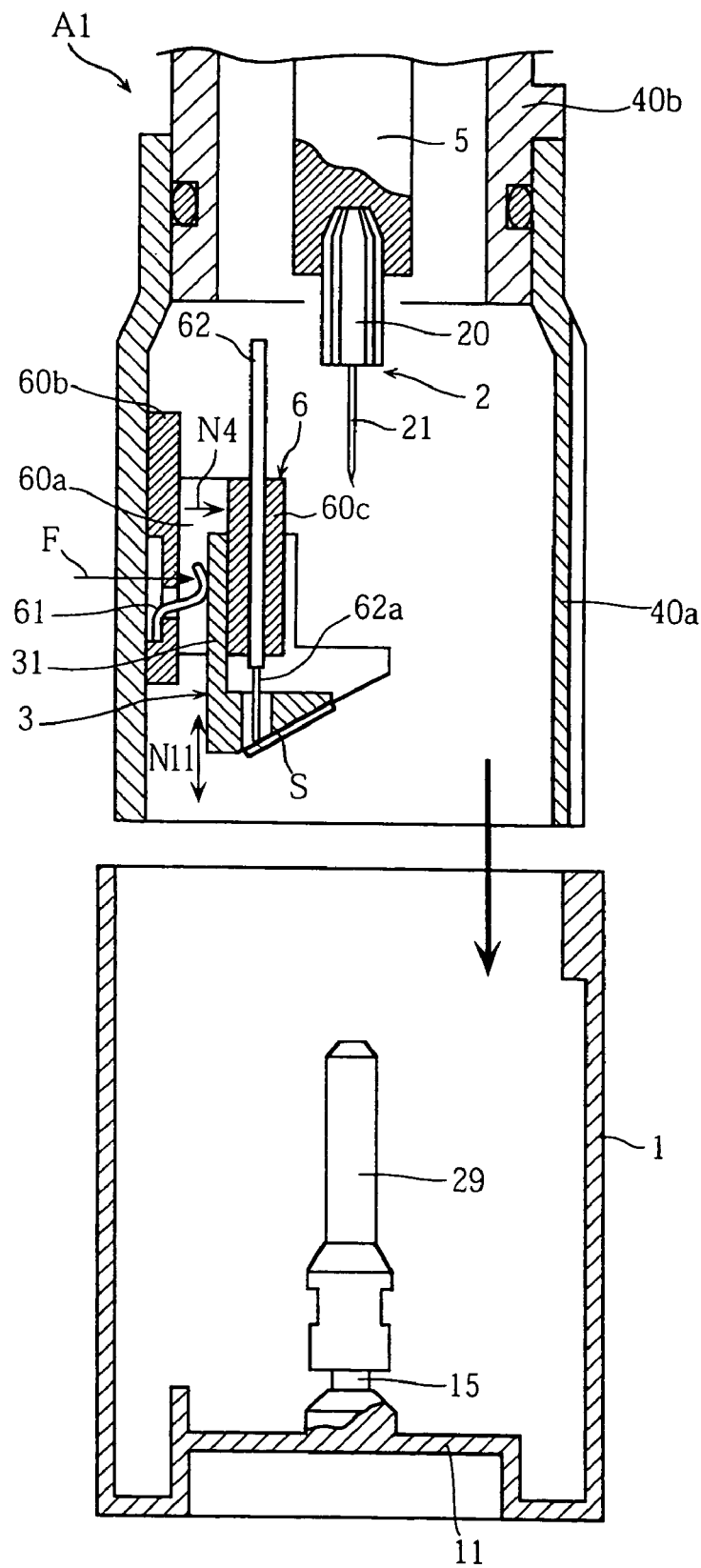
FIG. 14 is a sectional view showing a principal portion after the lancet and the sensor holder of the lancing unit shown in FIG. 1 are mounted to the lancing apparatus shown in FIG. 7.

The holding portion 6 serves to hold the sensor holder 3 and includes an attachment 60 fixed to the inner surface of the sleeve 40a. As better shown in FIG. 8, the attachment 60, which is made of synthetic resin, includes a first and a second walls 60b and 60c defining a space 60a. As shown in FIGS. 12 and 13, the space 60a is a portion for inserting the projecting wall 31 of the sensor holder 3 from below. The space 60a has a width s1 which is larger than the thickness t1 of the projecting wall 31 of the sensor holder 3. Therefore, when the projecting wall 31 of the sensor holder 3 attached to the case 1 is inserted into the space 60a, a gap 60a' is defined between the projecting wall 31 and the second wall 60c. However, when the projecting wall enters the space 60a, a spring 61 provided in the holding portion 6 exerts a resilient force F for pushing the projecting wall 31 toward the second wall 60c. Therefore, as shown in FIG. 14, when the sensor holder 3 and the cap 20 are separated from each other, the resilient force F of the spring 61 presses the projecting wall 31 against a side surface of the second wall 60c, whereby the sensor holder 3 is held by the holding portion 6. In the state shown in the figure, the sensor holder 3 is movable up and down along the side surface of the second wall 60c in the direction indicated by the arrow N11.

Figure 8:
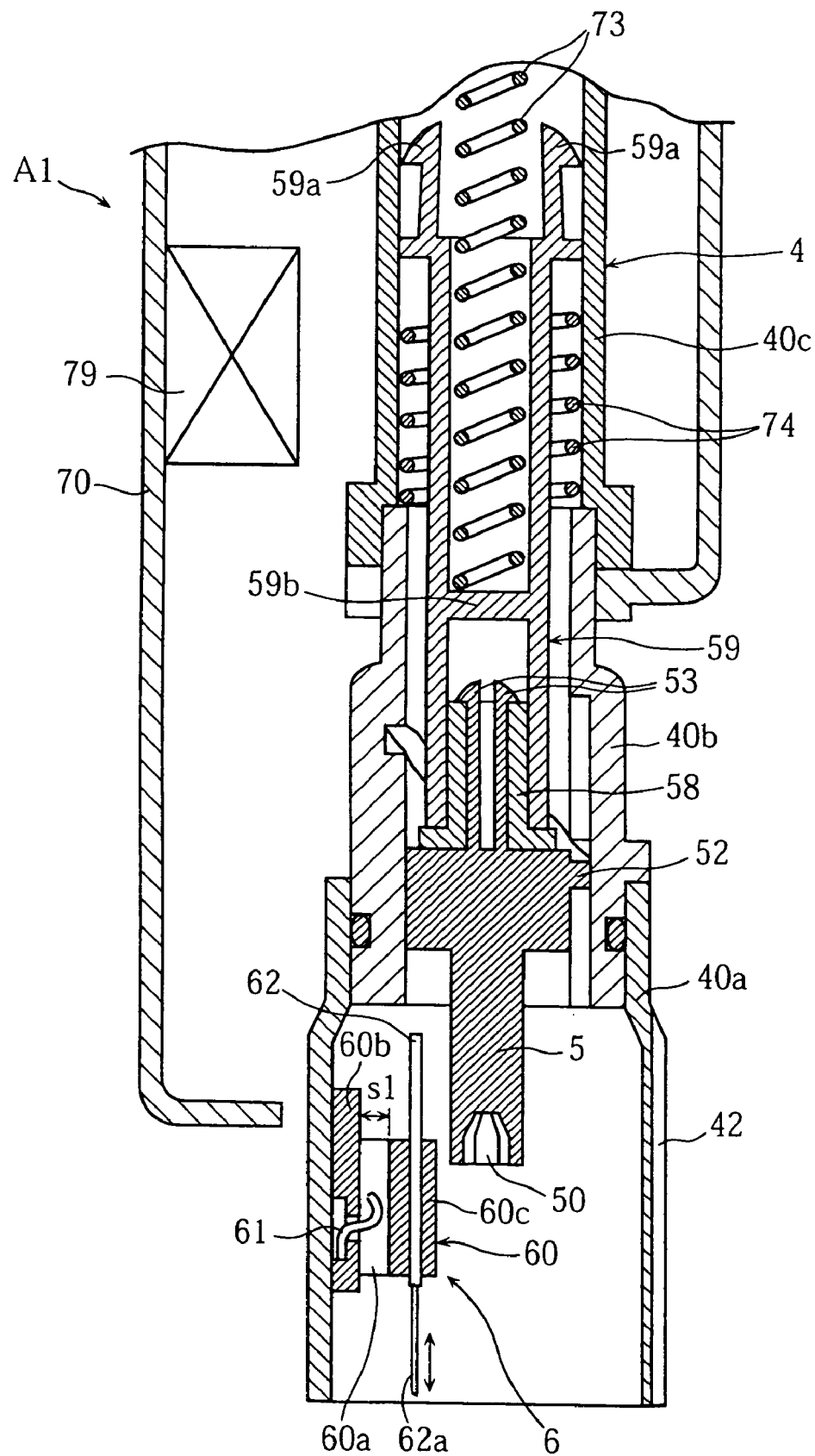
FIG. 8 is a sectional view of the principal portion of FIG. 7.

Referring to FIGS. 7 and 8, the paired measurement probes 62 are held in the second wall 60c of the holding portion 6. The paired measurement probes 62 for coming into contact with the paired electrodes 39b of the sensor S extend axially of the housing 4. Each of the measurement probes 62 has an expandable and contractible front end 62a which is extended downward by a resilient force of an appropriate spring (not shown) when the sensor holder 3 is not mounted to the lancing apparatus A1. As shown in FIGS. 12-14, when the sensor holder 3 is mounted to the holding portion 6, the front end 62a is pushed upward by the sensor S for contraction. The paired measurement probes 62 are electrically connected to a control circuit 79 provided in the outer case 70. The control circuit 79, which comprises e.g. a CPU and a memory attached thereto, performs computation of the glucose level in blood introduced to the reagent 39a based on the current detected via the paired measurement probes 62.

Figure 9:
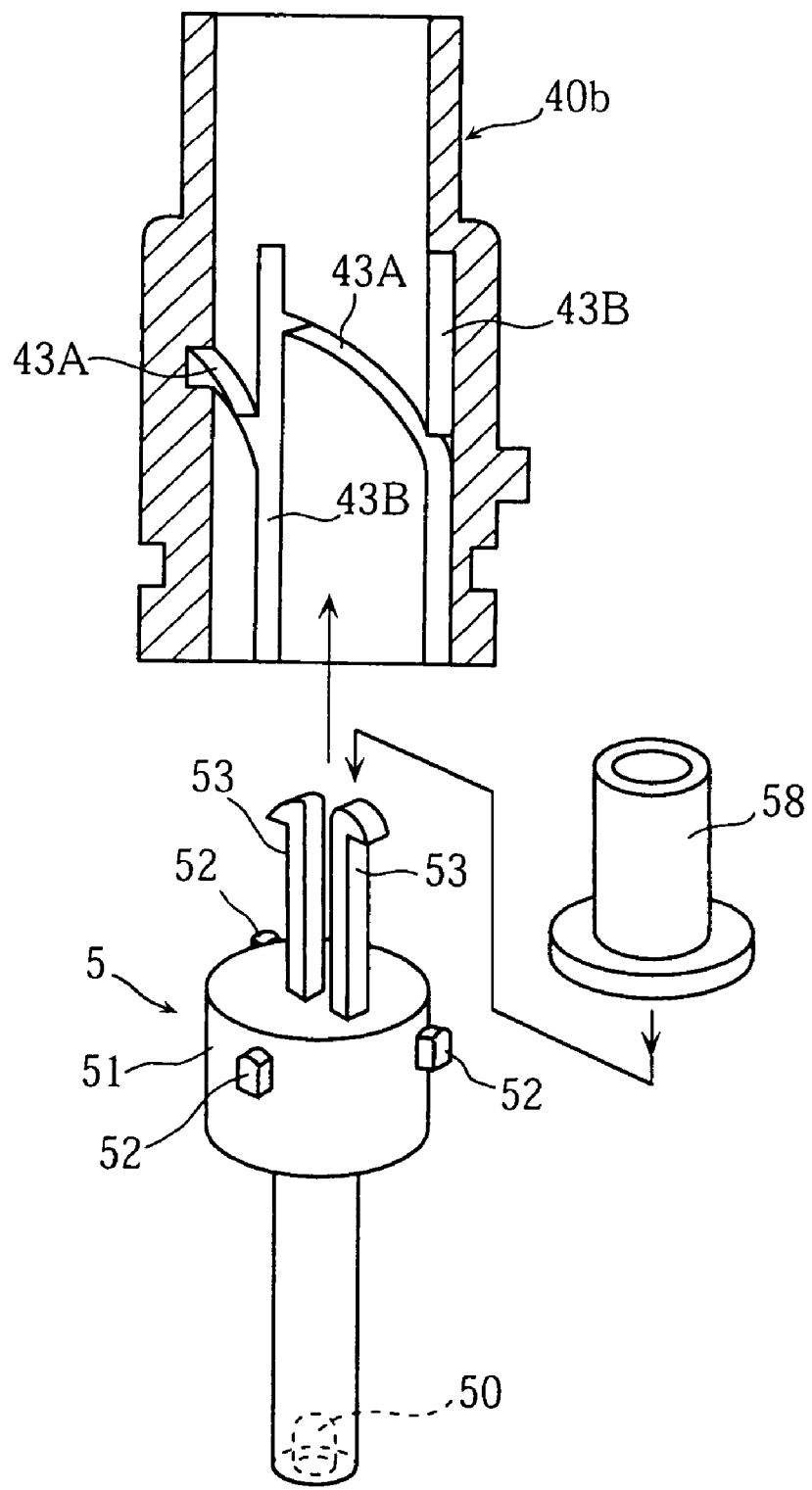
FIG. 9 illustrates the lancet holder and the intermediate sleeve for guiding the holder of the lancing apparatus shown in FIG. 7.

The lancet holder 5 is fitted in the sleeve 40b rotatably and slidably in the axial direction. The lancet holder 5 has a lower end formed with a recess 50. By pushing the body 20 of the lancet 2 into the recess 50, the lancet 2 is removably held by the lancet holder 5. The inside of the recess 50 is formed with a plurality of grooves into which the ribs 22 of the body 20 of the lancet 2 are fitted. With such an arrangement, when the body 20 of the lancet 2 is fitted into the recess 50, the relative rotation between the body 20 and the lancet holder 5 is prevented. As shown in FIG. 9, the lancet holder 5 has a head portion 51 having a circumferential surface formed with a plurality of equiangularly spaced projections 52. The projections 52 are fitted in and guided along a plurality of first guide grooves 43A and second guide grooves 43B formed at an inner wall surface of the sleeve 40b.

The first guide grooves 43A serve to rotate the lancet holder 5 when the lancet holder 5 is pushed upward by the lancet 2 of the lancing unit U1. The first guide grooves are inclined relative to the axial direction of the sleeve 40b. The second guide grooves 43B serve to guide the straight movement of the lancet 2 and the lancet holder 5 when these parts are caused to advance to lance the skin of a human body with the needle 21 of the lancet 2. The second guide grooves extend straight in the axial direction of the sleeve 40b. FIGS. 10A-10E are developed plan view of part of the first and the second guide grooves 43A and 43B, which are actually connected to each other. (In these figures, the nearby portions of the first and the second guide grooves 43A and 43B are cross hatched.) When the lancet holder 5 moves in the axial direction of the housing 4, the projections 52 move along the first and the second guide grooves 43A and 43B. The specific operation will be described later in detail.

As shown in FIGS. 7 and 8, the latch member 59 is connected to an upper portion of the lancet holder 5 and slidably accommodated in the housing 4. The latch member 59 has a lower end into which a bush 58 is non-rotatably fitted. In the bush 58, a plurality of projections 53 projecting from the upper surface of the lancet holder 5 are rotatably inserted. With such an arrangement, the lancet holder 5 is rotatable, whereas the latch member 59 does not rotate in accordance with the rotation of the lancet holder. The upper end of each of the projections 53 engages the upper end of the bush 58 so as not to drop therefrom, whereby the lancet holder 5 and the latch member 59 are connected to each other.

Figure 16:
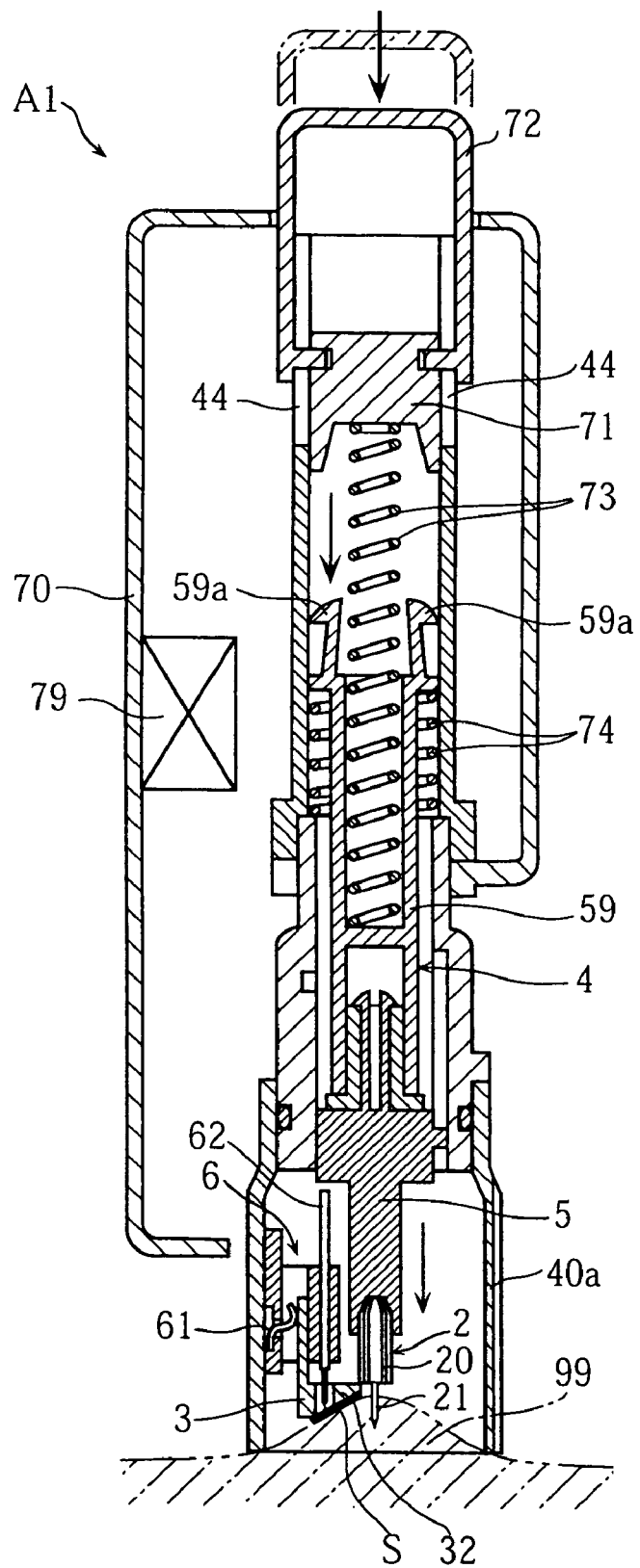
FIG. 16 is a sectional view showing an example of use of the lancing apparatus.

The latch member 59 has an upper portion formed with a pair of latch pawls 59a. Each of the latch pawls 59a serves to engage with an edge of a respective one of paired cutouts 44 formed in the sleeve 40c. As will be described later, this engagement occurs when the lancet holder 5 and the latch member 59 are pushed upward by the lancet 2 of the lancing unit U1. To the upper portion of the sleeve 40c are mounted a pusher 71 for releasing the latch, and an operation cap 72 connected to the pusher. Between the pusher 71 and an intermediate wall 59b of the latch member 59 is provided a spring 73. The spring 73 may comprise a compression coil spring, for example. The operation cap 72 is slidable relative to the sleeve 40c in the axial direction thereof. Thus, when the operation cap 72 is pushed down while compressing the spring 73, the pusher 71 also moves downward in accordance with the movement of the operation cap to press the latch pawls 59a. As a result, as shown in FIG. 16, the latch pawls 59a are forcibly disengaged from the edges of the cutouts 44, whereby the latch member 59 and the lancet holder 5 advance downward due to the resilient force of the compressed spring 73. In the housing 4 is also provided a return spring 74 for retreating the lancet holder 5 and the latch member 59 after the advancement.

The operation and advantages of the lancing unit U1 and the lancing apparatus A1 will be described below.

In the lancing unit U1 shown in FIGS. 1 and 2, the case 1 is hermetically closed by the film 14 before the use. Therefore, the reagent 39a of the sensor S is not exposed to e.g. moisture, whereby the quality deterioration in a short period of time is prevented. Since the needle 21 of the lancet 2 is covered by the cap 29 and the cap 29 is integrally formed on the body 20 of the lancet 2, the needle 21 is also hermetically sealed. Therefore, the sterilized state of the needle 21 can be properly maintained from the state before the lancet 2 is incorporated into the case 1. In manufacturing the lancing unit U1, the sterilization of the needle 21 can be completed before the sensor holder 3 is mounted to the cap 29. Therefore, the reagent 39a of the sensor S can be prevented from adversely affected by γ-rays used for the sterilization.

The lancing unit U1 is manufactured by mounting the lancet 2 provided with the cap 29 into the case 1, mounting the sensor holder 3 to the cap 29, and then sealing the opening 12 of the case 1 by the film 14. Therefore, the manufacture is easy. Specifically, the manufacture of the lancing unit U1 is easy particularly because the lancet 2 can be mounted just by fitting the hole 29a of the cap 29 to the projection 15 of the case 1 and the sensor holder 3 can be mounted just by fitting the paired holding walls 32b around the cap 29. In the lancing unit U1, particular parts for supporting the lancet 2 and the sensor holder 3 within the case 3 need not be additionally provided. Therefore, the total number of parts is relatively small, and the entire structure is relatively simple, so that the lancing unit U1 can be manufactured at low cost.

To use the lancing unit U1, the film 14 is broken or peeled off to expose the opening 12 of the case 1, and then the case 1 is fitted around the sleeve 40a of the lancing apparatus A1, as shown in FIG. 11. By this operation, the body 20 of the lancet 2 is fitted in the recess 50 of the lancet holder 5 to be held by the lancet holder 5. As the case 1 is slid upward in the direction indicated by the arrow N1, the lancet 2 pushes the lancet holder 5 upward. As a result, the lancet holder 5 and the body 20 rotate in the direction indicated by the arrow N2, whereby the boundary portion between the lancet 2 and the cap 29 is twisted and broken.

Figure 10A:
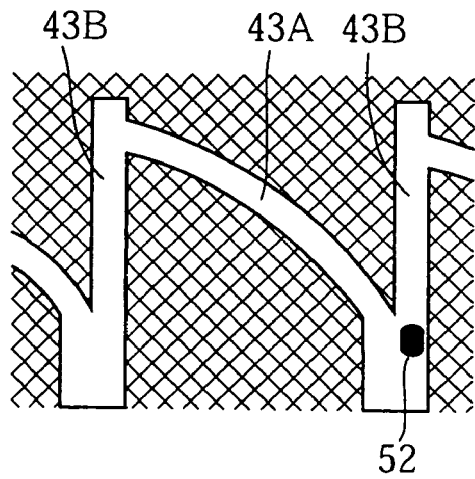
FIGS. 10A-10E illustrate the guiding of the projections of the lancet holder shown in FIG. 9.
Figure 10B:
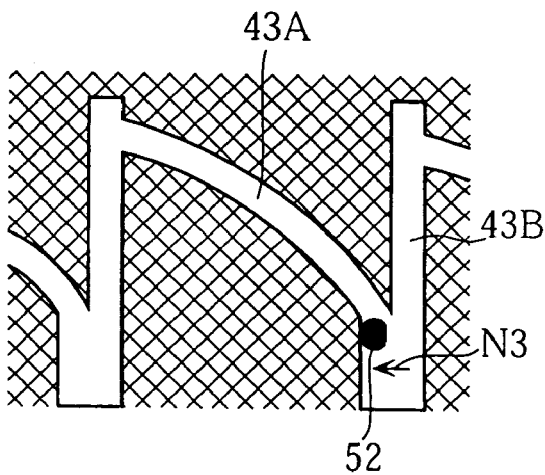

Specifically, as shown in FIG. 10A, the projections 52 of the lancet holder 5 are initially located within the second guide grooves 43B. When the lancet 2 is fitted into the recess 50, the projections 52 move closer to the first guide grooves 43A, as indicated by the arrow N3 in FIG. 10B. To cause this movement, either the front ends of the ribs 22 of the body 20 of the lancet 2 or the grooves in the recess 50 of the lancet holder 5 are inclined to be helical so that the lancet holder 3 rotates in the direction indicated by the arrow N3 through a slight angle when the body 20 is fitted into the recess 50.

Figure 10C:
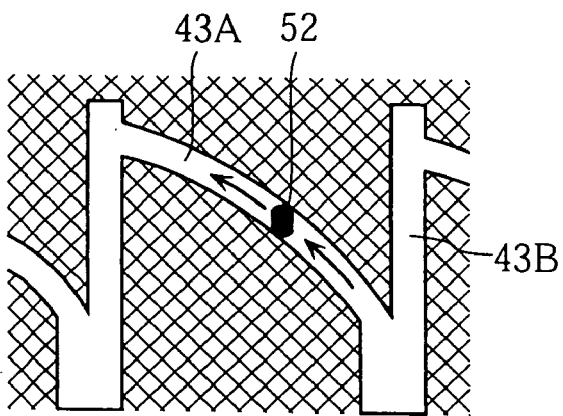
Figure 10D:
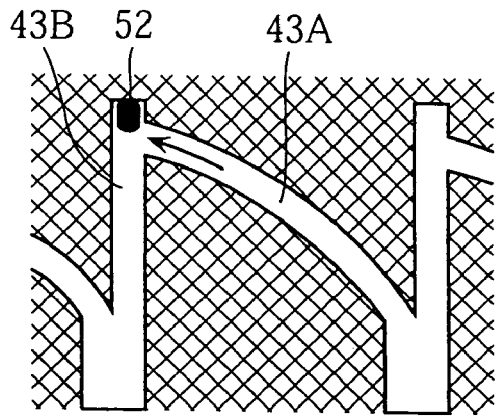

Subsequently, when the lancet holder 5 is pushed upward by the lancet 2, the projections 52 move along the first guide grooves 43A, as shown in FIGS. 10C and 10D. This operation causes the lancet holder 5 to rotate, whereby the body 20 of the lancet 2 also rotates. On the other hand, the cap 29 of the lancing unit U1 does not rotate because it is fixed to the case 1. Therefore, the boundary portion 28 between the body 20 of the lancet 2 and the cap 29 is twisted, whereby the boundary portion 28 is broken.

As shown in FIG. 12, when the case 1 is pushed upward by an appropriate amount, the latch member 59 also moves upward, whereby each of the latch pawls 59a engages with an edge of a respective one of the cutouts 44. Thus, the latch member 59 is latched. As shown in FIG. 13, when the case 1 is pushed upward, the projecting wall 31 of the sensor holder 3 enters the space 60a of the holding portion 6. In this embodiment, each portion of the lancing unit U1 can be accurately positioned relative to a corresponding portion of the lancing apparatus A1 by sliding and fitting the case 1 relative to the sleeve 40a while preventing the rotation, whereby a high positioning accuracy can be provided. Therefore, even when the space 60a has a relatively small opening width, the projecting wall 31 of the sensor holder 3 can be guided precisely into the space 60a. Moreover, the above-described fitting of the lancet 2 into the recess 50 of the lancet holder 5 can be performed precisely.

When the projecting wall 31 enters the space 60a, the projecting wall 31 receives the resilient force F of the spring 61. When the sensor holder 3 is supported by the cap 29, the sensor holder keeps its posture while resisting the resilient force F, whereby the gap 60a' is kept between the second wall 60c and the projecting wall 31. The front end 62a of each measurement probe 62 is pushed upward by the sensor S and exerts a resistive force to the pushing. This resistive force can be utilized for reliably bringing the measurement probe 62 into contact with the relevant electrode 39b. In this embodiment, however, the measurement probe 62 does not come into contact with the electrode 39b of the sensor S when the projecting wall 31 just enters the space 60a. As will be described later, such contact is established when the sensor holder 3 and the sensor S move toward the center of the housing 4.

After the pushing up of the case 1 is completed in the above-described manner, the case 1 is pulled down for detachment from the sleeve 40a, as shown in FIG. 14. Since the boundary portion 28 between the body 20 of the lancet 2 and the cap 29 has been twisted and broken as noted above, the lancet 2 and the cap 29 readily separate from each other when the case 1 is pulled. By this separation, the lancet 2 is duly mounted to the lancet holder 5 with the needle 21 exposed. When the case 1 is pulled down, the cap 29 slides relative to the sensor holder 3 and pulled out to locate below the sensor holder 3. Thus, the sensor holder 3 separated from the cap 29 is secured to the holding portion 6.

As noted above, in the lancing unit U1 and the lancing apparatus A1, the mounting of the lancet to the lancet holder 5, the separation of the cap 29 from the lancet 2, the mounting of the sensor holder 3 to the holding portion 6, the separation of the cap 29 from the lancet holder 5, and the latching of the latch member 59 can be performed just by fitting the case 1 around the sleeve 40a by sliding the case by an appropriate amount and then pulling out the case, which is convenient. Since the cap 29 is kept fixed to the case 1, these parts can be easily disposed of.

In this embodiment, only the lancet 2 and the sensor holder 3 are mounted to the lancing apparatus 1, so that the lancing apparatus A1 need not be designed to hold the case 1, for example. Therefore, the size reduction of the lancing apparatus A1 is possible. Specifically, in the prior art apparatus, not only the lancing member and the auxiliary parts but also the support member for supporting them are mounted to the lancing apparatus. In this embodiment, however, a member corresponding to such a support member is not mounted to the lancing apparatus, so that the lancing apparatus of this embodiment can be made smaller than the prior art apparatus. Moreover, in this embodiment, the lancet 2 is solely mounted to the reciprocally-movable lancet holder 5 of the lancing apparatus A1. In the prior art apparatus, the lancing member need be slidably mounted to a predetermined member (first housing 91A) of the lancing unit. Since such need does not exist in this embodiment, the structure of the lancing unit can be simplified, and the lancing member reliably operates properly when mounted to the lancing apparatus.

When sensor holder 3 and the cap 29 are separated each other by pulling out the case 1 from the sleeve 40a, the projecting wall 31 of the sensor holder 3 is pressed against the second wall 60c by the resilient force F of the spring 61. As a result, the sensor holder 3 moves toward the center of the sleeve 40a (in the direction indicated by the arrow N4 in FIG. 14) by the amount corresponding to the dimension of the gap 60a' shown in FIG. 13. As a result, the sensor S comes into contact with the measurement probes 62. With such an arrangement, the electrical conduction between the sensor S and the measurement probes 62 can be suspended until the proper mounting of the sensor holder 3 is completed, whereby wasteful power consumption can be prevented. Moreover, by moving the sensor holder 3 toward the center of the sleeve 40a, the sensor S comes close to the lancing position, which provides the following advantages.

Figure 15:
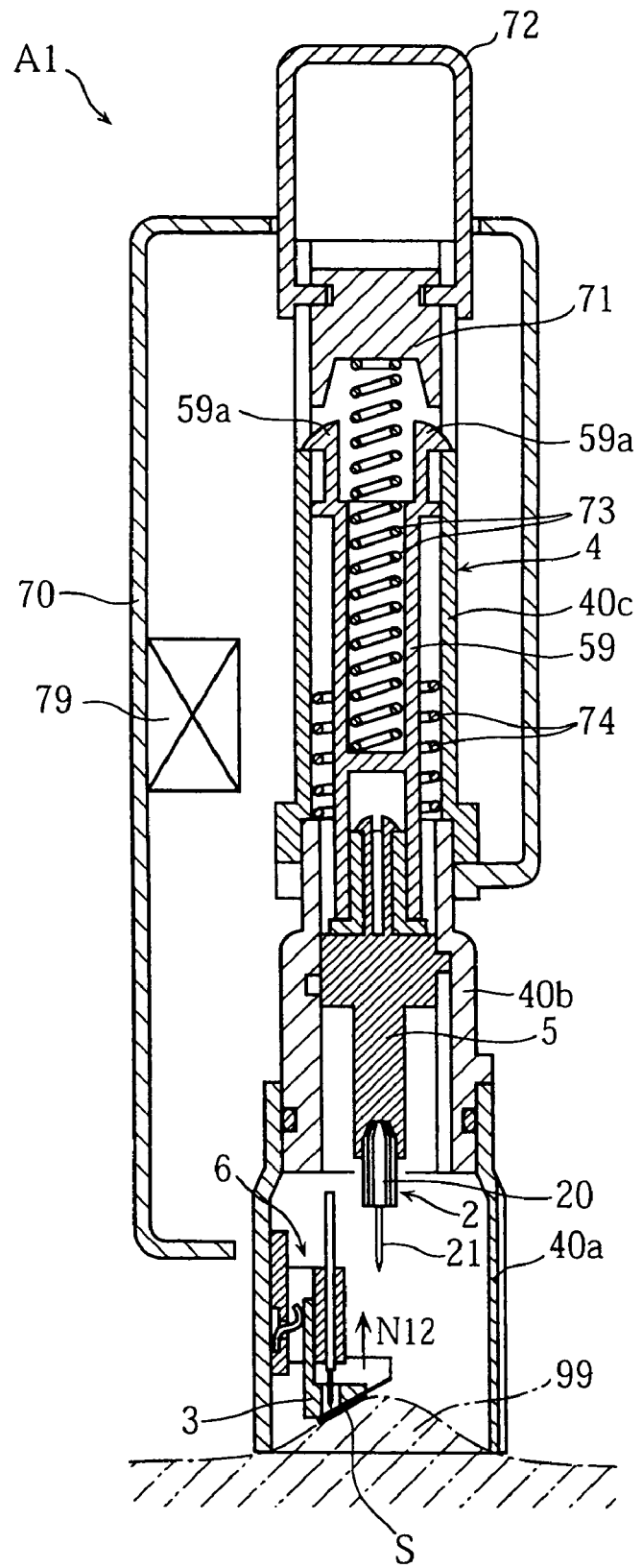
FIG. 15 is a sectional view showing an example of use of the lancing apparatus.

As shown in FIG. 15, after the lancet 2 and the sensor holder 3 are mounted to the lancing apparatus A1 by the above process, the front end of the sleeve 40a of the lancing apparatus A1 is brought into contact with the skin 99 of a human body as the object to be lanced. When the sleeve 40a is brought into contact with the skin 99, the skin 99 may bulge. When the skin 99 bulges, the sensor holder 3, which is made movable upward, is lifted as indicated by the arrow N12. Therefore, the sensor holder 3 does not hinder the bulging of the skin 99. The bulging amount of the skin 99 becomes relatively large when a negative pressure is generated in the sleeve 40a by using a pump, as will be described later. The arrangement of the sensor holder 3 to be movable upward is particularly advantageous in such a case.

Figure 10E:
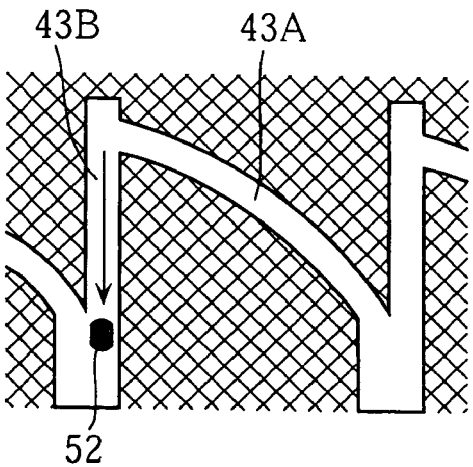

Subsequently, the operation cap 72 is pushed to advance the pusher 71. As a result, as shown in FIG. 16, each of the latch pawls 59a is disengaged from the edge of the relevant cutout 44, whereby the latch member 59 and the lancet holder 5 move downward by the resilient force of the spring 73 to cause the needle 21 of the lancet 2 to lance the skin 99. At this time, the body 20 of the lancet 2 partially engages the main body 32 of the sensor holder 23, whereby the needle 21 is prevented from sticking deep into the skin 99 more than necessary. As shown in FIG. 10E, when the lancet holder 5 moves downward, the projections 52 move along the second guide grooves 43B, whereby the lancet holder 5 can move straight. As a result of the straight movement, the projections 52 can be located at a position which is similar to the initial position shown in FIG. 10A, which enables the repeating of the above operation.

After the needle 21 lances the skin 99, the latch member 59 and the lancet holder 5 immediately retreat by a predetermined amount due to the resilient force of the return spring 74 to pull out the needle 21 from the skin 99. Preferably, a pump or a pump mechanism is provided in the lancing apparatus A1 to generate a negative pressure in the sleeve 40a in lancing the skin. With such an arrangement, the negative pressure promotes the bleeding from the skin 99, so that the lancing amount of the needle 21 of the lancet 2 can be reduced, which is advantageous for reducing the damage to the skin 99.

The blood extracted from the skin 99 is applied to the sensor S and guided to the reagent 39a of the sensor S. As described with reference to FIG. 14, the sensor holder 3 has approached the center of the sleeve 40a, i.e. located closer to the lancing position, so that the blood can be reliably applied to a predetermined portion of the sensor S. Therefore, the amount of blood guided to the reagent 39a can be prevented from becoming insufficient.

As means for positioning the sensor holder 3 close to the center of the sleeve 40a, it may be considered to mount the sensor holder 3 close to the center of the case 1 from the first in the state of the lancing unit U1 shown in FIGS. 1 and 2. However, since the sensor holder 3 is supported by the cap 29 in the lancing unit U1, the wall thickness of the cap 29 need be reduced for positioning the sensor holder 3 close to the center of the case 1. When the wall thickness of the cap 29 is excessively reduced, the mechanical strength of the cap may be deteriorated. In such a case, the cap 29 may not reliably support the sensor holder 3. In this embodiment, however, such a problem can be avoided, because the sensor holder 3 moves closer to the center of the sleeve 40a when it is mounted to the lancing apparatus A1.

In this embodiment, the distance between the lancet 2 and the sensor holder 3 in the state of the lancing unit U1 can be set relatively large. Therefore, it is not necessary to take the trouble to reduce the distance between the lancet 2 and the sensor holder 3 in designing and manufacturing the unit. Moreover, since the movement of the lancet 2 toward the lancing position is performed by detaching the cap 29 from the lancet 2, the user need not perform any additional operation for that purpose, which is convenient.

After the lancing operation is performed, the control circuit 79 computes the glucose level in blood. In the lancing apparatus A1, the computed value may be displayed at a display (not shown) such as a liquid crystal display, for example. The lancet 2 and the sensor holder 3 after use are detached from the lancing apparatus A1 and disposed of. Preferably, such detachment is performed by using a tool or a member which is designed to enter the sleeve 40a to engage and hold the lancet 2 and the sensor holder 3. In such a case, the user need not directly touch the lancet 2 and the sensor holder 3 after use.

Figure 17:
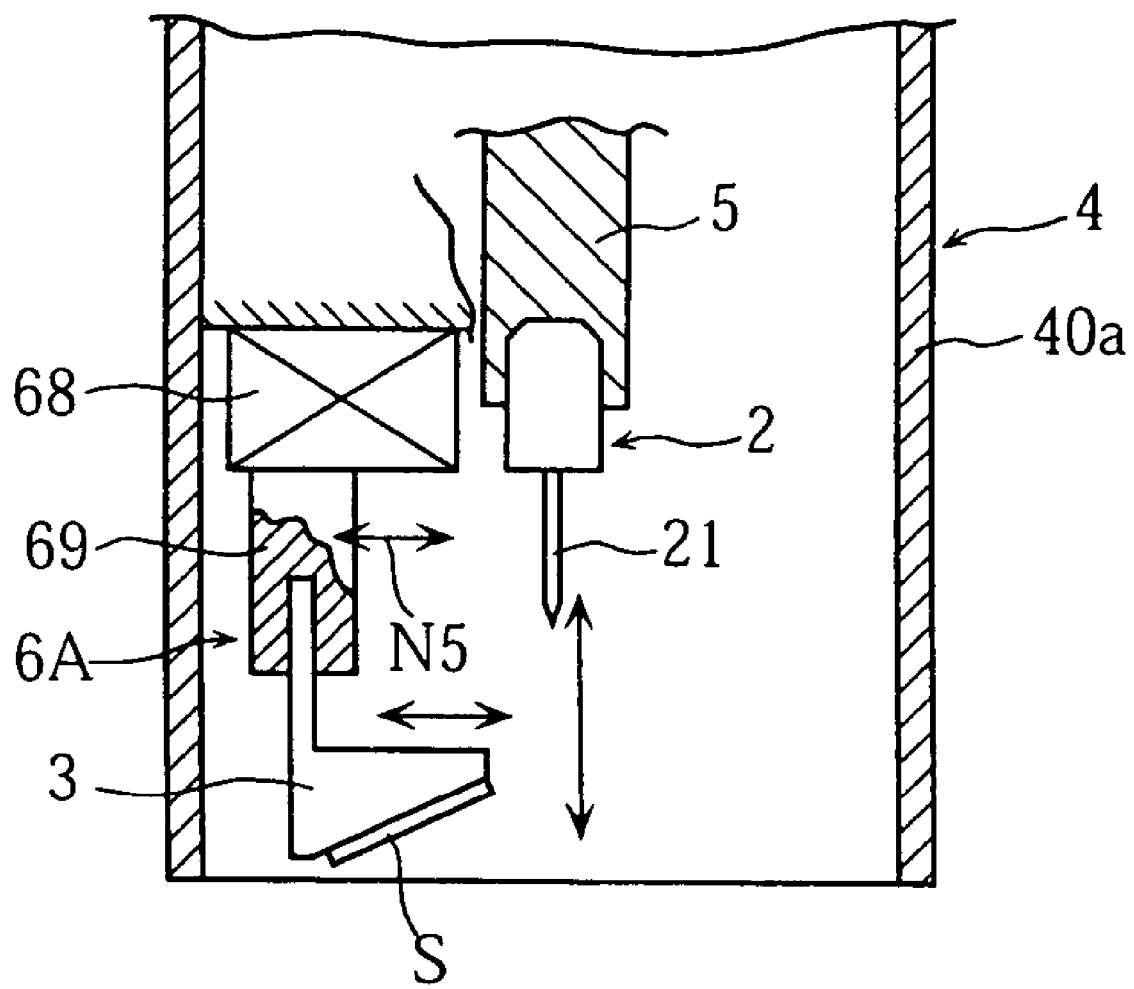
FIG. 17 is a sectional view of a principal portion of another example of lancing apparatus according to the present invention.

FIG. 17 is a sectional view showing a principal portion of another example of lancing apparatus according to the present invention. In FIG. 17 and the subsequent figures, the elements which are identical or similar to those of the foregoing embodiment are designated by the same reference signs as those used for the foregoing embodiment.

The holding portion 6A of the lancing apparatus shown in the figure includes a supporting element 69 for removably supporting the sensor holder 3. The supporting element is reciprocally movable, by a driving force of a driver 68, in a direction (indicated by the arrow N5) crossing the direction of the reciprocal movement of the lancet 2. As the driver 68, use may be made of various kinds of devices such as a small-sized linear motor or an actuator utilizing an electromagnetic force which can cause the reciprocal movement.

With such an arrangement, the distance between the supporting element 69 and the lancet holder 5 can be kept relatively large before the lancet 2 and the sensor holder 3 are mounted to the lancet holder 5 and the supporting element 69, respectively. Such a large distance facilitates the mounting of the lancet 2 and the sensor holder 3 when these members are mounted one by one. Further, the possibility that the user's hand touches the needle 21 of the lancet 2 by mistake in mounting the sensor holder 3 can be reduced. After the lancet 2 and the sensor holder 3 are mounted, the supporting element 69 is moved at an appropriate timing to move the sensor holder 3 close to the advancing movement path of the lancet 2, i.e. close to the lancing position. Thus, the advantages intended by the present invention are duly obtained. In this way, in the present invention, driving means other than a spring may be utilized for moving the auxiliary part (sensor holder 3 in this embodiment) in a direction crossing the advancing direction of the lancet.

Figure 18:
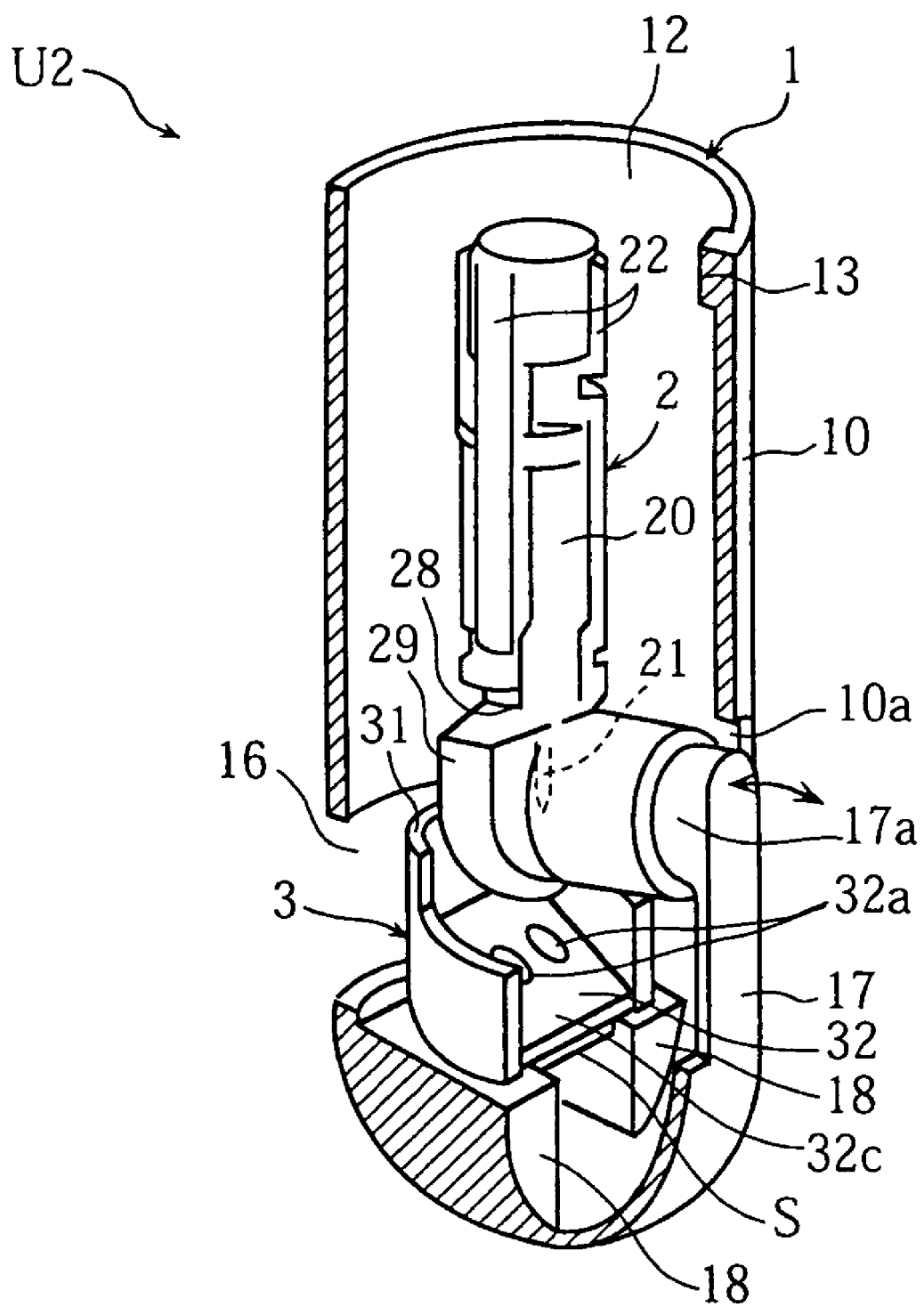
FIG. 18 is a perspective view, partially cut away, showing another example of lancing unit according to the present invention.
Figure 19:
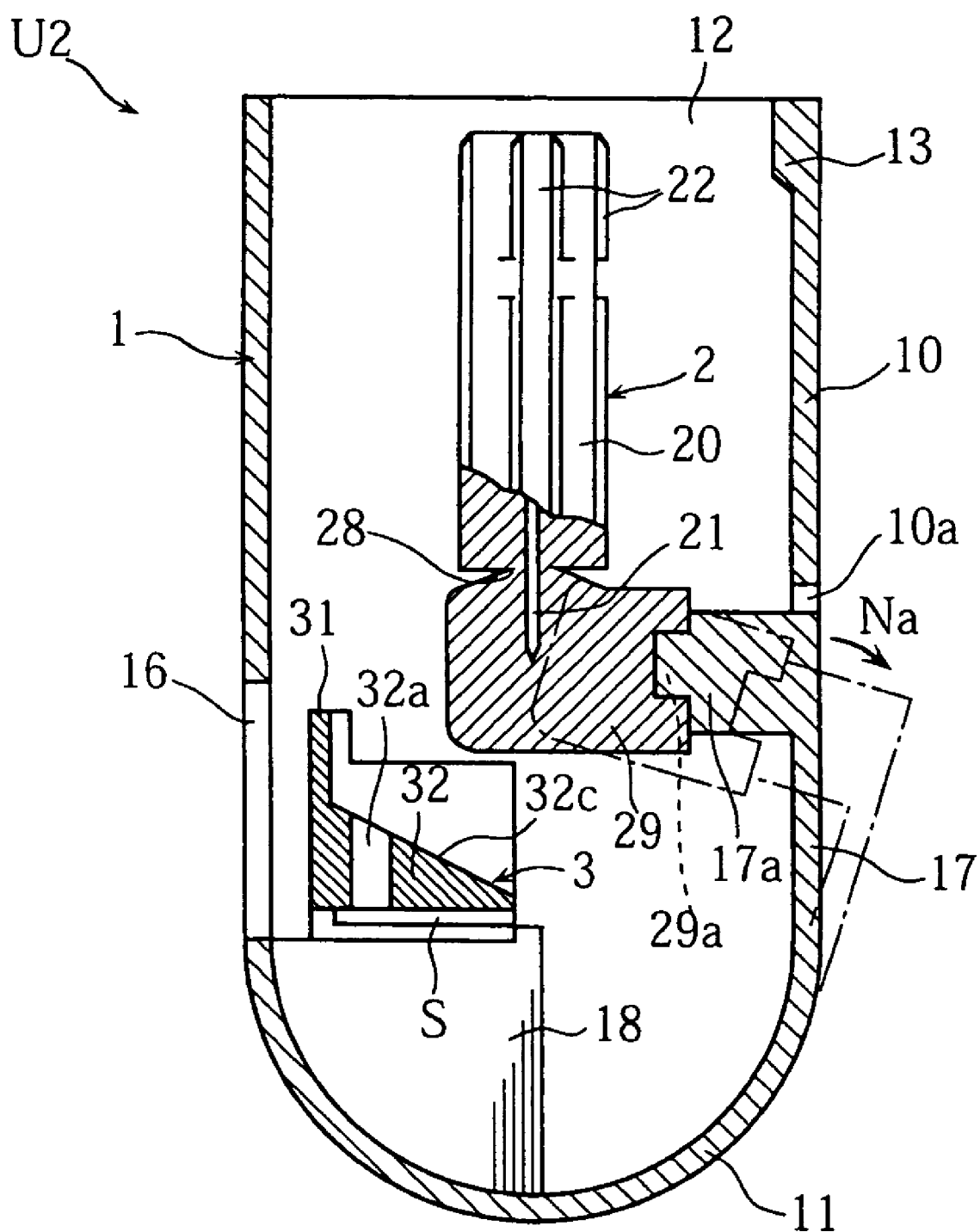
FIG. 19 is a side sectional view of FIG. 18.

FIGS. 18 and 19 show another example of lancing unit according to the present invention. The lancing unit U2 in this embodiment includes a case 1 accommodating a lancet 2, a cap 29 and a sensor holder 3, and this point is similar to the lancing unit U1 of the above-described embodiment. However, the sensor holder 3 is arranged below the cap 29 so that the cap 29 is interposed between the sensor holder 3 and the lancet 2. Thus, the three members, i.e. the lancet 2, the cap 29 and the sensor holder 3 are generally aligned in the axial direction of the tubular portion 10 of the case 1.

The cap 29 is formed integrally on the body 20 of the lancet 2 and supported under the body 20 by the case 1. Specifically, the cap 29 is supported by an arm 17 provided at the case 1. The arm 17 is provided by forming a cutout 10a in the tubular portion 10 of the case 1 and has a lower end connected to the tubular portion 10 and an upper end which is a free end. The upper end of the arm 17 is formed with a boss 17a for partially fitting into a recess 29a formed at a side surface of the cap 29. The cap 29 is bonded to the boss 17a with an adhesive, for example. As shown by phantom lines in FIG. 19, the arm 17 is flexibly deformable, with elastic restoring force, in the direction indicated by the arrow Na, i.e. in a direction crossing the axial direction (vertical direction in the figure) of the tubular portion 10. By the flexible deformation of the arm 17 in the arrow Na direction, the cap 29 can move to a position where the cap does not overlap the sensor holder 3 in the axial direction of the tubular portion 10.

The sensor holder 3 is placed on and supported by a seat portion 18 provided at a bottom portion 11 of the case 1. Part of the sensor S is located directly below the cap 29. The sensor holder 3 is detachable upward from the seat portion 18. However, to prevent the sensor holder 3 from easily moving on the seat portion 18 or dropping from the seat portion 18, the sensor holder 3 is held in engagement with the seat portion 18 by non-illustrated engagement means or bonded to the seat portion 18 with a relatively low adhesive strength. The circumferential wall of the tubular portion 10 is formed with an opening 16 so that the incorporation of the sensor holder 3 into the case 1 can be performed by utilizing the opening 16. The main body 32 of the sensor holder 3 has an upper surface 32c which is inclined to be progressively lower as it extends toward the central axis of the case 1.

The lancing unit U2 is hermetically sealed with a wrapping member (not shown) such as a gas-impermeable wrapping film. Specifically, in this hermetical sealing, the entirety of the lancing unit U2 is wrapped by the wrapping member, because the case 1 provided with the cutout 10a cannot be hermetically sealed just by closing the opening 12 by the wrapping member.

FIGS. 20-25 show an example of lancing apparatus suitable for using the above lancing unit U2 and the relevant items.

Figure 20:
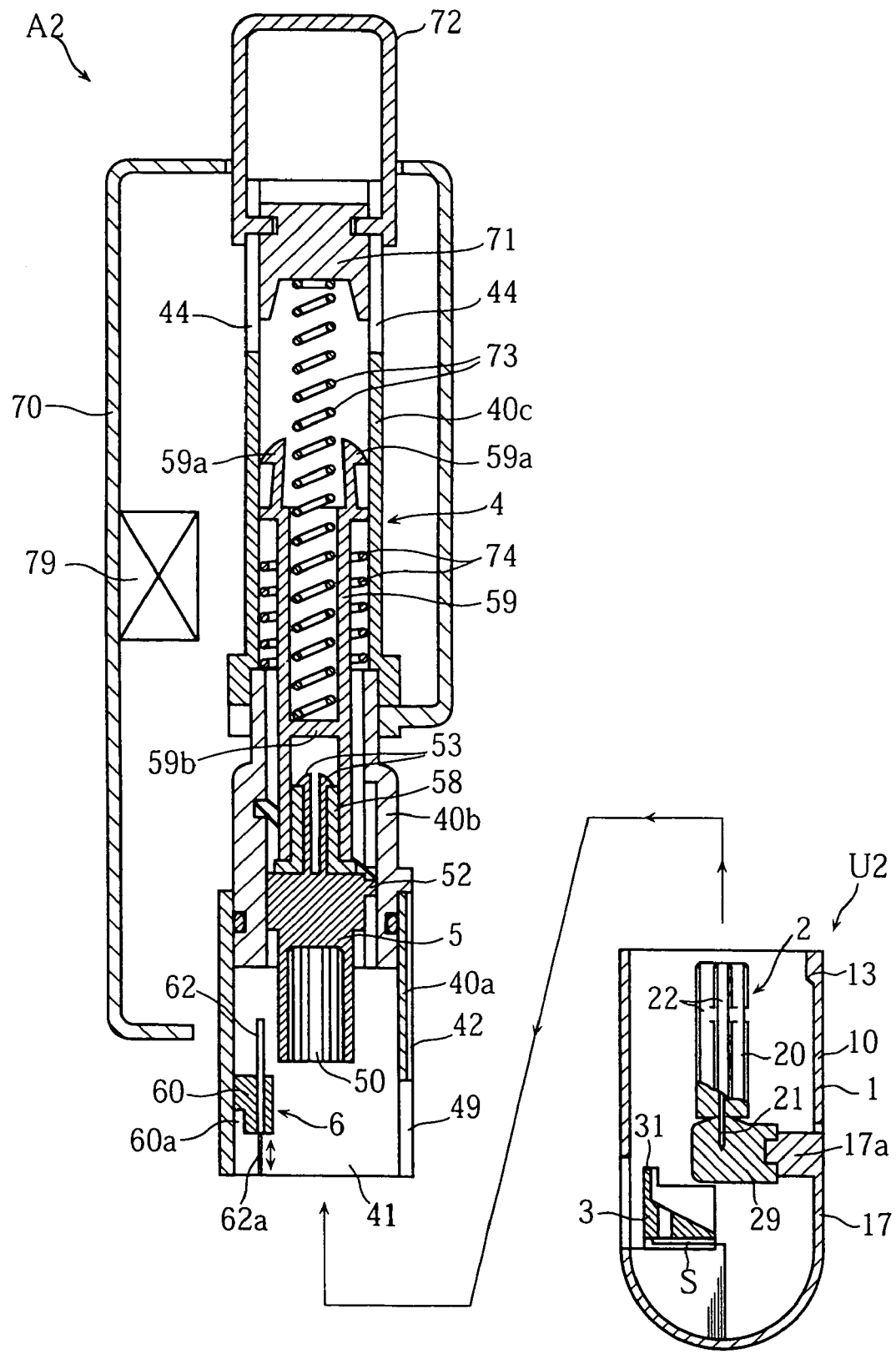
FIG. 20 is a sectional view showing another example of lancing apparatus according to the present invention.

As better shown in FIG. 20, the lancing apparatus A2 in this embodiment includes a housing 4, a lancet holder 5, a latch member 59 and a holding portion 6, and the basic structure is similar to that of the lancing apparatus A1. However, the sleeve 40a of the housing 4 of this embodiment is formed with a cutout 49. The cutout 49 is provided to prevent the interference between the sleeve 40a and the boss 17a of the arm 17 when the case 1 of the lancing unit U2 is fitted around the sleeve 40a.

The holding portion 6 includes a downwardly open space 60a and is capable of holding the sensor holder 3 with an appropriate holding force when the projecting wall 31 of the sensor holder 3 is inserted into the space 60a. Though not illustrated, holding of the sensor holder 3 may be performed by pressing the projecting wall 31 against a wall defining the space 60a with the use of a suitable spring, clamping the projecting wall 31 with a suitable clamp member, or bringing the projecting wall 31 into engagement with the holding portion 6, for example. Unlike the foregoing embodiment, the sensor holder 3 in this embodiment is not moved toward the center of the sleeve 40a after it is held by the holding portion 6. Therefore, the holding portion 6 can be designed to fixedly hold the sensor holder 3 as it is when the sensor holder approaches the holding portion.

Next, the operation and advantages of the lancing unit U2 and the lancing apparatus A2 will be described.

Since the lancing unit U2 is similar in structure to the lancing unit U1 except the difference in positional relationship between the cap 29 and the sensor holder 3, many advantages which are similar to those of the lancing unit U1 can be obtained. Since the lancing unit U2 is entirely wrapped with a wrapping member, exposure of the sensor S to e.g. moisture can be reliably prevented.

Figure 21:
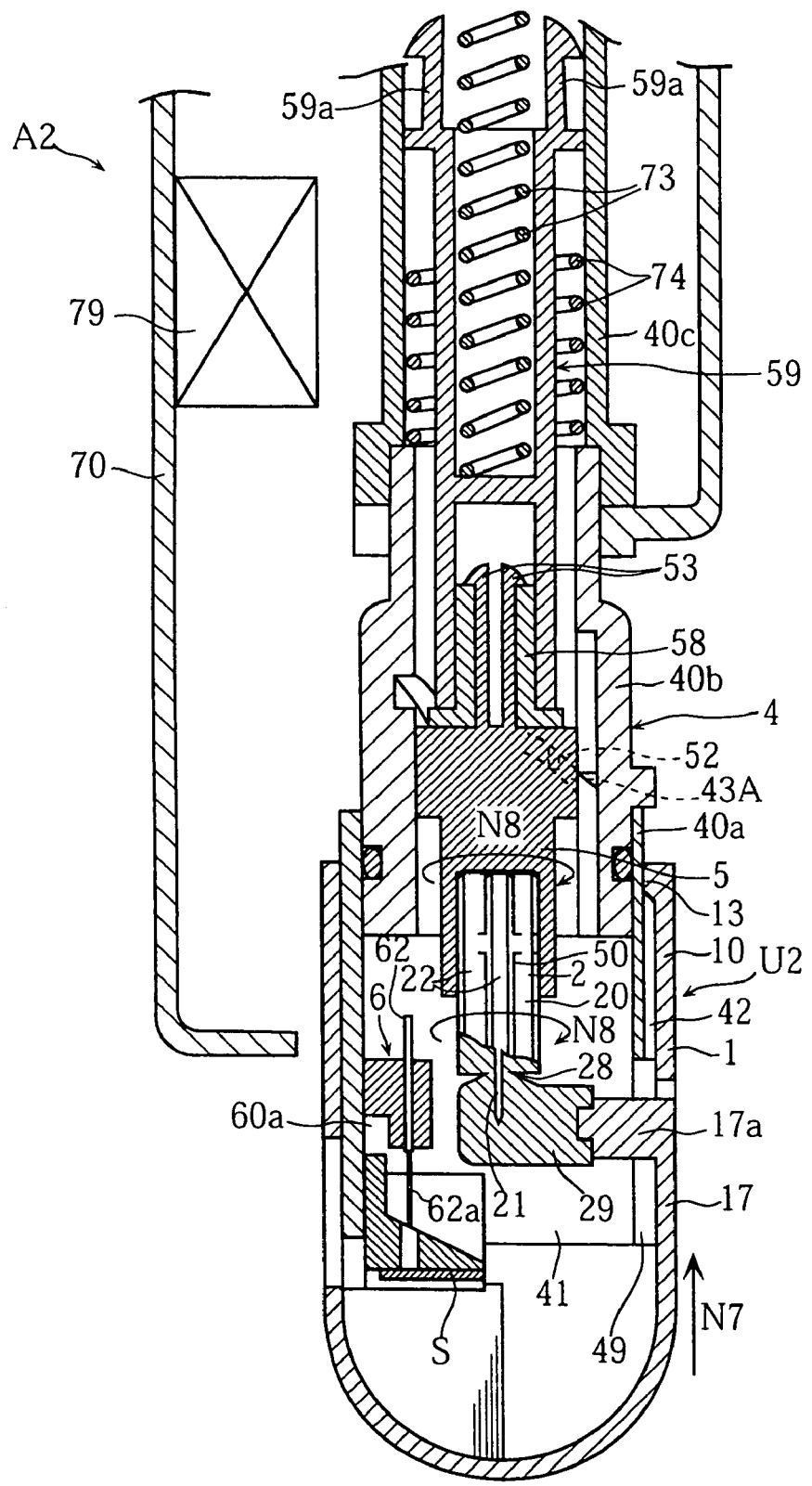
FIG. 21 is a sectional view of a principal portion in the process of mounting the lancet and the sensor holder of the lancing unit shown in FIG. 18 to the lancing apparatus shown in FIG. 20.
Figure 22:
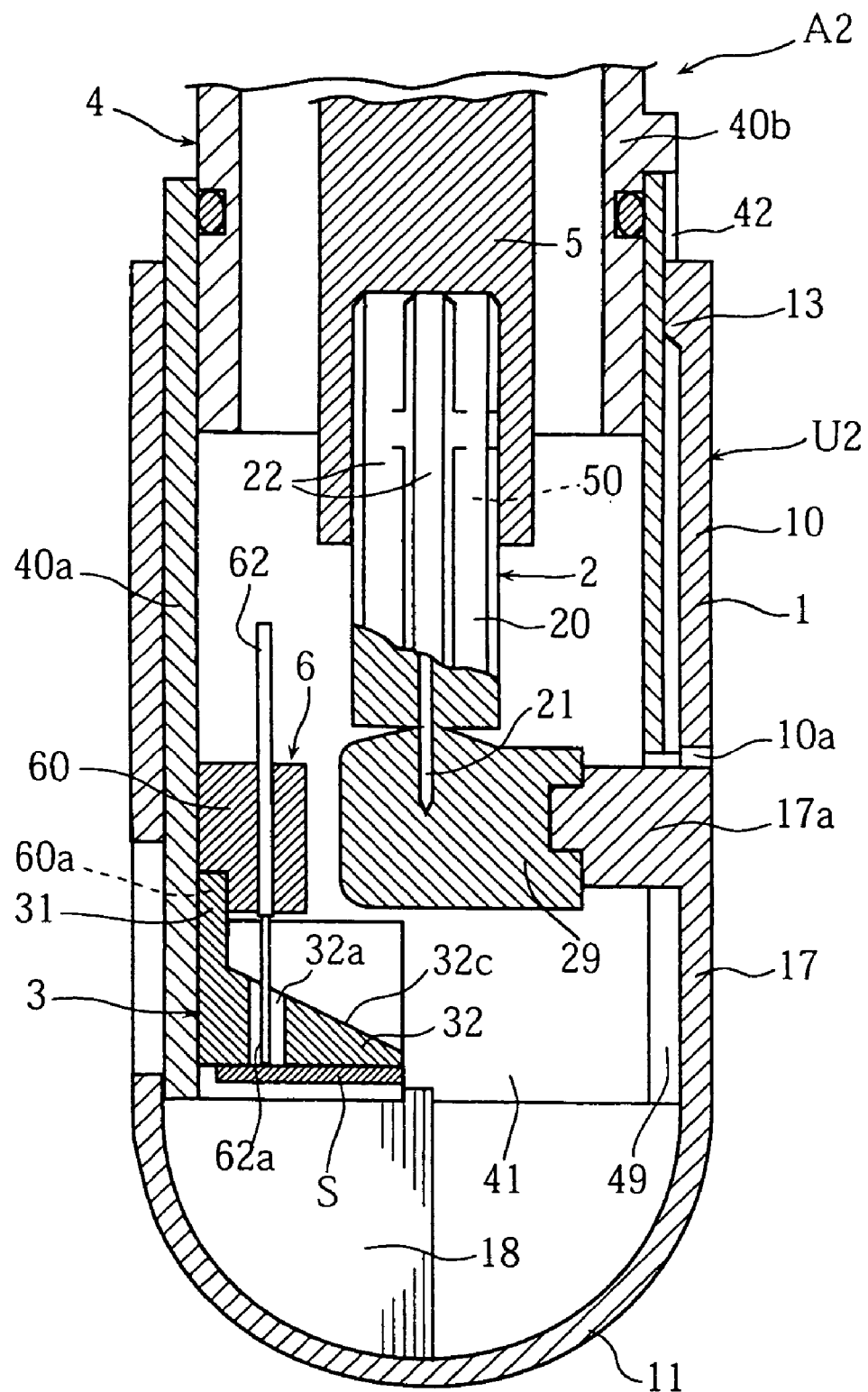
FIG. 22 is a sectional view of a principal portion of the lancing apparatus shown in FIG. 20 in which the lancet and the sensor holder of the lancing unit shown in FIG. 18 are held.

To use the lancing unit U2, the operations which are similar to those for using the lancing unit U1 are performed. Specifically, first, as shown in FIG. 21, the case 1 is fitted around the sleeve 40a of the lancing apparatus A2 and pushed upward in the direction indicated by the arrow N7. By this operation, the body 20 of the lancet 2 is fitted and retained in the recess 50 of the lancet holder 5, and the lancet holder 5 and the body 20 of the lancet 2 rotate in the direction indicated by the arrow N8, whereby the boundary portion 28 between the lancet 2 and the cap 29 is twisted and broken. As shown in FIG. 22, the projecting wall 31 of the sensor holder 3 enters the space 60a to be held by the holding portion 6.

Figure 23:
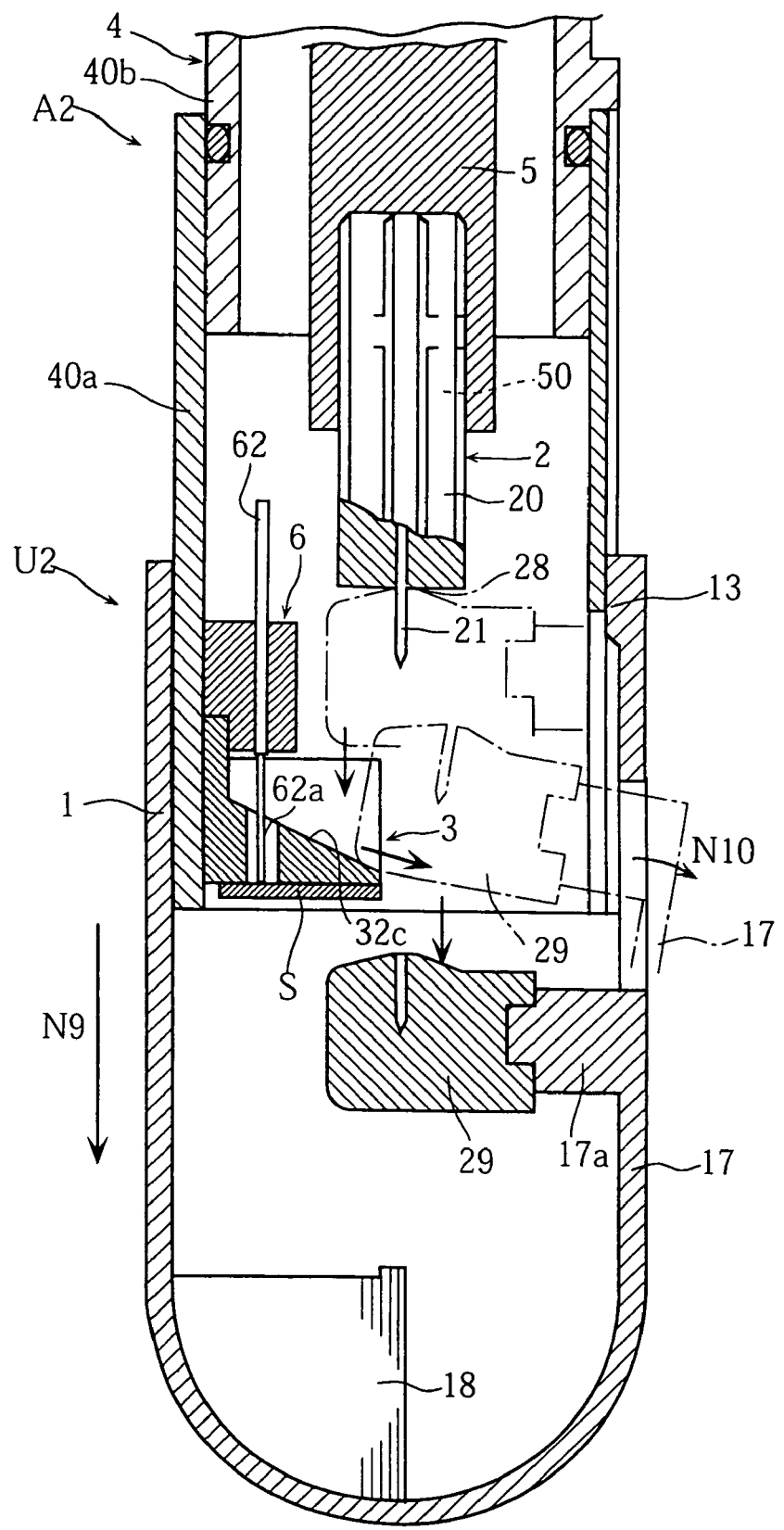
FIG. 23 is a sectional view of a principal portion for showing the operation of pulling off the case of the lancing unit shown in FIG. 18 from the lancing apparatus shown in FIG. 20.

When the case 1 is thereafter moved downward in the direction indicated by the arrow N9 in FIG. 23, the cap 29 and the lancet 2 are duly separated from each other. By the separation, the lancet 2 is duly held by the lancet holder 5 with the needle 21 exposed, whereas the cap 29 is kept mounted to the case 1. The sensor holder 3 is separated from the seat portion 18 of the case 1 and held by the holding portion 6.

Figure 24:
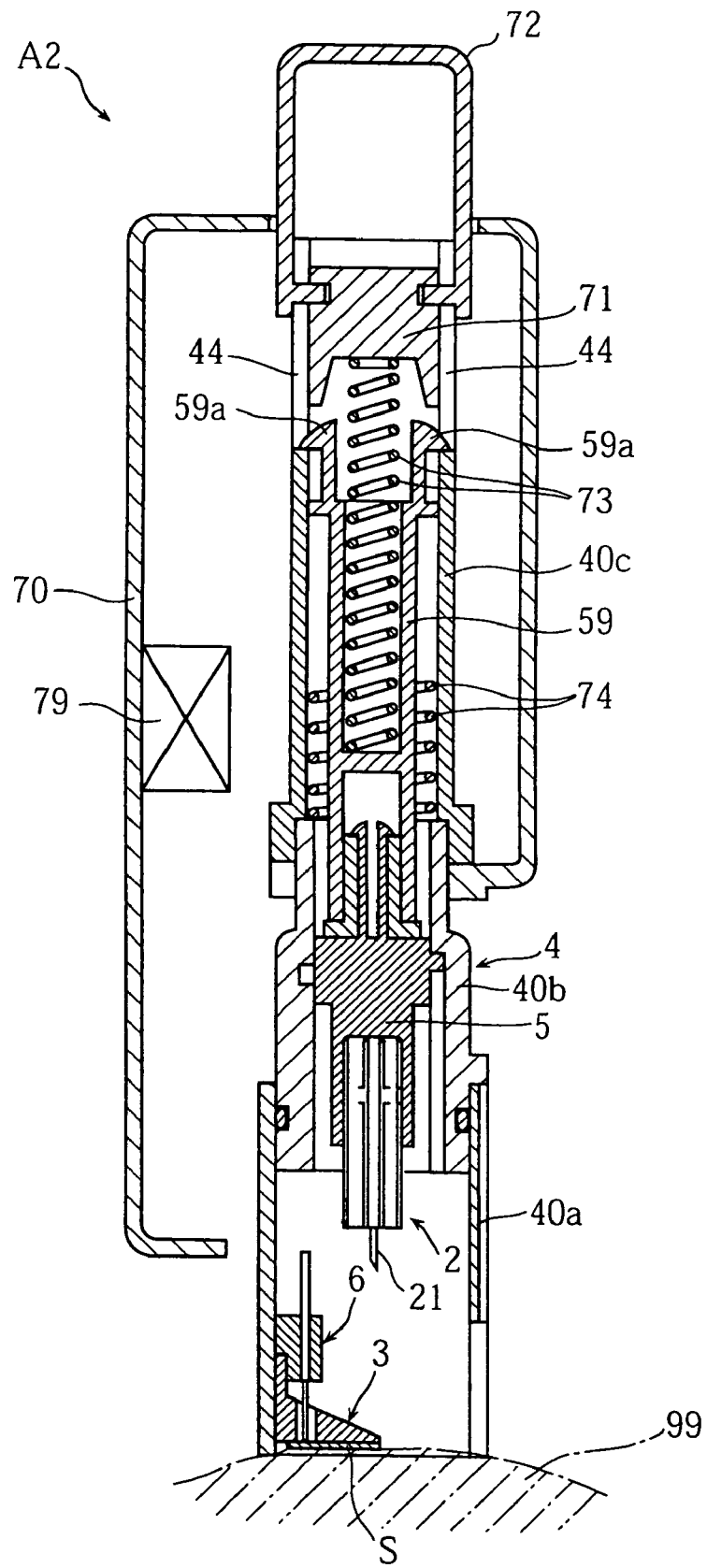
FIG. 24 is a sectional view showing the state after the mounting of the lancet and the sensor holder to the lancing apparatus of FIG. 20 is completed.

As shown by phantom lines in FIG. 23, in lowering the case 1, the cap 29 partially engages the upper surface 32c of the sensor holder 3. By this engagement, the arm 17 is flexed in the direction indicated by the arrow N10. The cap 29 flexed in this way passes beside the sensor holder 3 to be located below the sensor holder 3. In the arrangement of this embodiment, the cap 29 engages the upper surface 32c after the cap 29 is completely separated from the needle 21 of the lancet 2. With such an arrangement, bending of the needle 21 by the cap 29 is reliably prevented. Since the inclined upper surface 32c of the sensor holder 3 serves to guide the movement of the cap 29 in the direction indicated by the arrow N10, the passing of the cap 29 beside the sensor holder 3 is performed smoothly. In this way, by preventing the cap 29 from interfering with the sensor holder 3, the case 1 can be smoothly detached from the lancing apparatus A2. FIG. 24 shows the lancing apparatus A2 after the above operations.

Figure 25:
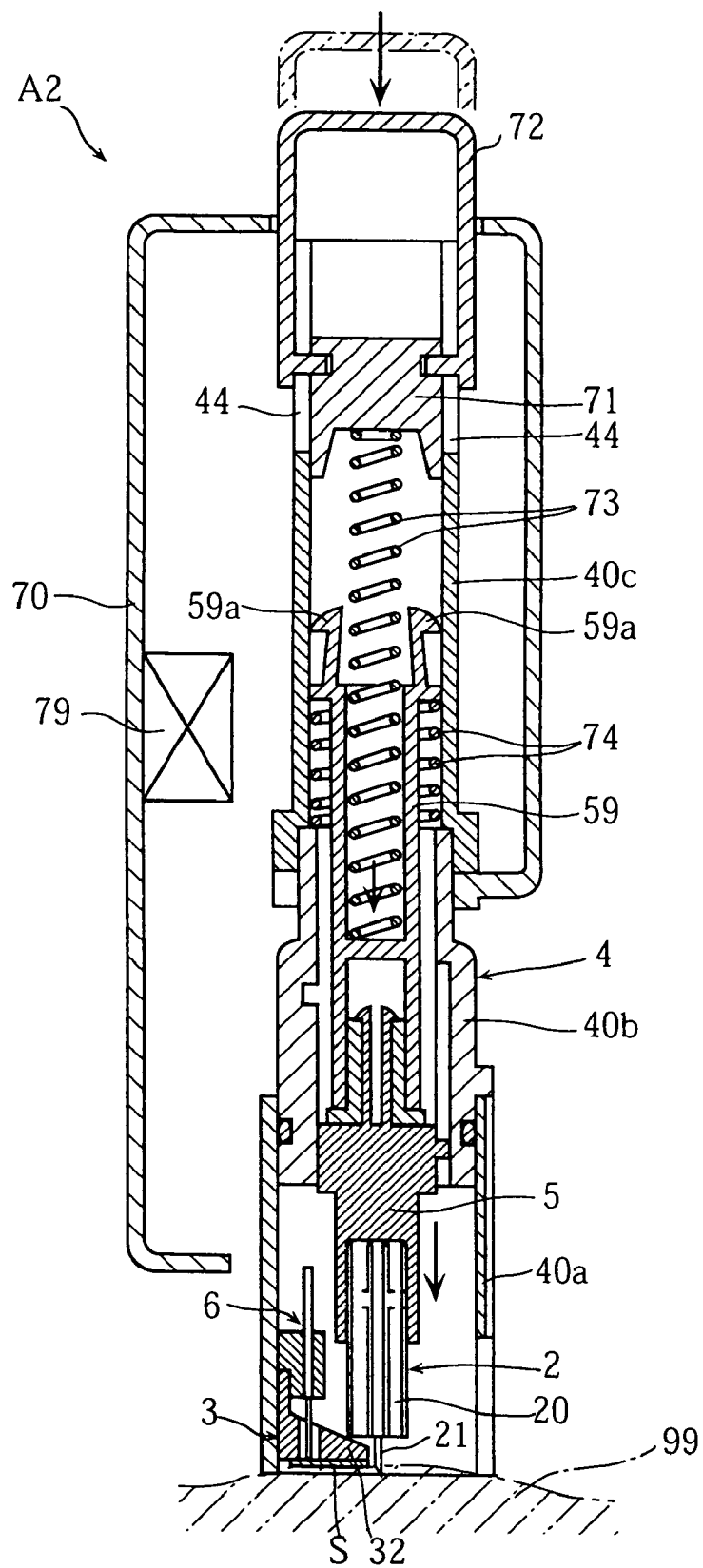
FIG. 25 is a sectional view showing the lancing operation of the lancing apparatus shown in FIG. 20.
Figure 26A:
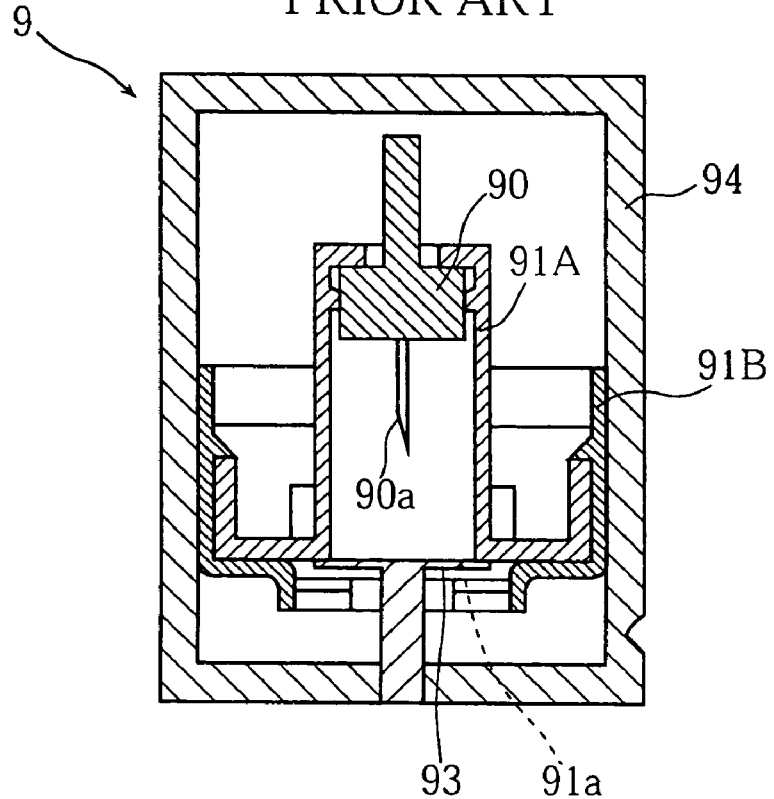
Figure 26B:
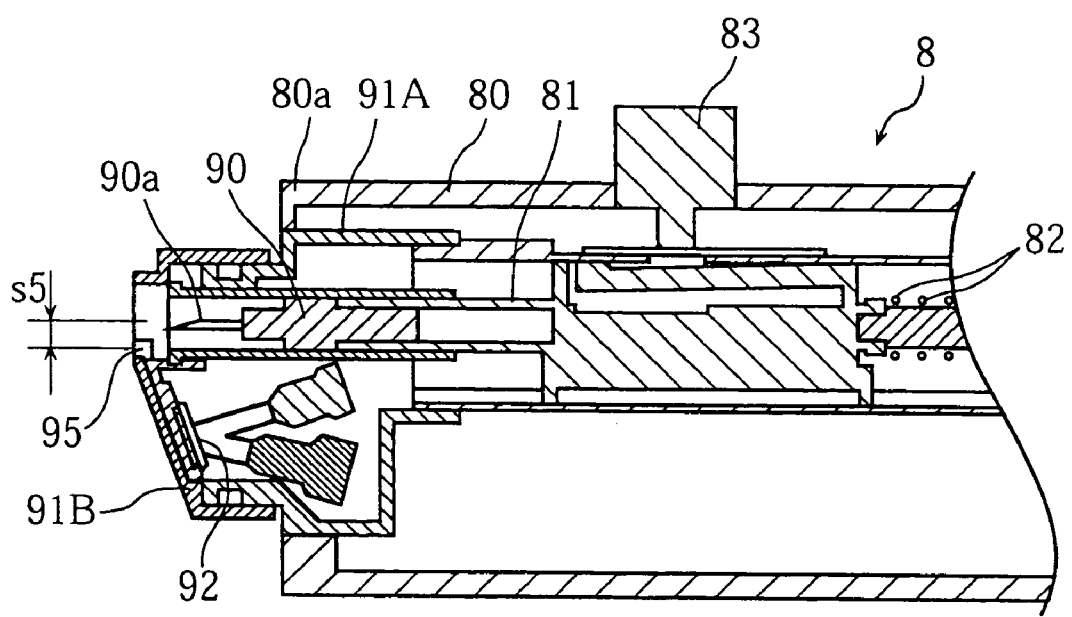
FIG. 26B is a sectional view showing a prior art lancing apparatus.

As shown in the figure, the lancet 2 and the sensor holder 3 are so mounted to the lancing apparatus A2 as to partially overlap each other in the axial direction of the housing 4. With this arrangement, the sensor S can be located close to the center of the housing 4. Therefore, as shown in FIG. 25, when the lancet 2 is moved downward to lance the skin 99, the sensor S is located close to the lancing position. As a result, similarly to the foregoing embodiment, the blood bleeding from the skin 99 is reliably introduced to the sensor S. Since the body 20 engages the sensor holder 3 when the lancet 2 moves downward, the lancing depth of the needle 21 in the skin 99 can be controlled.

In this embodiment, the sensor holder 3 is mounted close to the center of the housing 4 from the first. Therefore, unlike the foregoing embodiment, it is unnecessary to move the sensor holder 3 toward the center of the housing 4. Therefore, the mechanism of the holding portion 6 can be made simple. Moreover, the opening width of the front end of the housing 4 can be made relatively small, which is advantageous for reducing the size of the lancing apparatus A2.

The present invention is not limited to the foregoing embodiments. Specific structure of each part of the lancing unit and the lancing apparatus according to the present invention may be modified in various ways.

The auxiliary part in the present invention may not comprise a sensor holder to which a sensor provided with a reagent is mounted. For example, the auxiliary part may comprise a sensor itself provided with e.g. a reagent, and the sensor by itself may be supported by the supporter. The auxiliary part may comprise a part just for taking the sample obtained by lancing. Further, the auxiliary part need not necessarily comprise a part utilized for analyzing the sample. For example, the auxiliary part may comprise a part just for engaging the lancing member in lacing to control the lancing depth into the skin.

The supporter of the lancing unit may comprise a member other than a case having a cylindrical portion. As the lancing member, use may be made of a member having a structure which is different from that of the above-described lancet. Although it is preferable that the cap for covering the needle of the lancing member is integrally formed on the body of the lancing member by resin molding as is in the foregoing embodiments, the present invention is not limited thereto. For example, the cap may be bonded to the body of the lancing member with an adhesive, for example. The cap may be formed integrally on the supporter. The cap, the supporter, and the body of the lancing member may be integral with each other. The body of the lancing member and the cap may be separated from each other just by a pulling force, instead of by twisting as a result of the relative rotation. As a method for separating the lancing member and the cap from each other by twisting, the lancing member may be non-rotatably mounted to the lancing apparatus, and the user may manually rotate the supporter (case) for causing the relative rotation between the lancing member and the cap. Such a method eliminates the need for providing the lancing apparatus with means for rotating the lancing member, which leads to a reduction in manufacturing cost of the lancing apparatus.

The lancing unit and the lancing apparatus of the present invention are not limited to those used for measuring the glucose level in blood but may be structured for use in other kinds of measurement and analysis.

In the lancing apparatus according to the present invention, the holder for holding the lancing member may be provided with a mechanism for clamping the lancing member, for example. Further, instead of a coil spring, other biasing means may be utilized in the moving mechanism for advancing the holder for holding the lancing member.

The invention claimed is:

1. A lancet supplying unit comprising a case having a closed bottom and a closable open top, a lancing member housed in the case, a sensor housed in the case and provided separately from the lancing member, and a supporter detachably supporting each of the lancing member and the sensor in the housing,
   wherein the case is temporarily attached to a lancing apparatus for supplying the lancing member and the sensor to the lancing apparatus,
   wherein the lancing member and the sensor remain attached to the lancing apparatus even after the case is detached from the lancing apparatus,
   wherein the lancing member includes a needle,
   wherein the lancet supplying unit further comprises a cap for covering the needle, the cap being detachable from the lancing member,
   wherein the lancing member is supported by the supporter via the cap, and
   wherein the cap is integrally formed on the supporter.

2. The lancet supplying unit according to claim 1, wherein the sensor is held by a sensor holder, and wherein, when lancing of a skin is performed by utilizing the lancing member, the sensor holder engages the lancing member to control lancing depth in the skin.

3. The lancet supplying unit according to claim 1, wherein the lancing member includes a body holding the needle, and wherein the cap is integrally formed on the body.

4. The lancet supplying unit according to claim 3, wherein a boundary portion between the cap and the body has a structure which causes a stress to be concentrated on the boundary portion more than on other portions of the cap and the body.

5. The lancet supplying unit according to claim 4, wherein the boundary portion has a constricted configuration.

6. The lancet supplying unit according to claim 1, wherein the supporter includes a portion for fitting to a part of the cap to hold the cap in a standing posture.

7. The lancet supplying unit according to claim 1, wherein the case includes a tubular portion for accommodating the cap together with the lancing member and the sensor.

8. The lancet supplying unit according to claim 1, further comprising a lid for closing the open top the case.

9. The lancet supplying unit according to claim 1, wherein a direction in which the sensor is detachable from the supporter corresponds to a direction in which the cap is detachable from the lancing member.

10. The lancet supplying unit according to claim 1, wherein the sensor is detachably supported by the cap.

11. A lancet supplying unit comprising a case having a closed bottom and a closable open top, a lancing member housed in the case, a sensor housed in the case and provided separately from the lancing member, and a supporter detachably supporting each of the lancing member and the sensor in the housing,
   wherein the case is temporarily attached to a lancing apparatus for supplying the lancing member and the sensor to the lancing apparatus,
   wherein the lancing member and the sensor remain attached to the lancing apparatus even after the case is detached from the lancing apparatus,
   wherein the lancing member includes a needle,
   wherein the lancing supplying unit further comprises a can for covering the needle, the cap being detachable from the lancing member,
   wherein the cap is supported by the supporter while being interposed between the lancing member and the sensor in a first direction in which the needle of the lancing member extends, the cap being movable in a second direction crossing the first direction to avoid overlapping with a holder retaining the sensor in the first direction.

12. The lancet supplying unit according to claim 11, wherein the supporter includes an arm portion for supporting the cap, the arm portion being deformable in the second direction.

13. The lancet supplying unit according to claim 12, wherein the arm portion is provided by forming a cutout in the supporter.

14. The lancet supplying unit according to claim 12, wherein the holder retaining the sensor includes a surface facing the cap, the surface being inclined at least partially to be oriented also in the second direction.

15. A lancet supplying unit comprising a lancing member, an auxiliary part which is separate from the lancing member, and a supporter detachably supporting each of the lancing member and the auxiliary part, wherein the lancing member includes a needle, wherein the lancet supplying unit further comprises a cap detachable from the lancing member for covering the needle, wherein the cap is supported by the supporter while being interposed between the lancing member and the auxiliary part in a first direction in which the needle of the lancing member extends, the cap being movable in a second direction crossing the first direction to avoid overlapping with the auxiliary part in the first direction.

\* \* \* \* \*